United States Patent
Ofuji et al.

(10) Patent No.: US 10,499,872 B2
(45) Date of Patent: Dec. 10, 2019

(54) RADIATION DETECTION APPARATUS, RADIATION DETECTION SYSTEM, AND METHOD FOR CONTROLLING RADIATION DETECTION APPARATUS

(71) Applicant: CANON KABUSHIKI KAISHA, Tokyo (JP)

(72) Inventors: Masato Ofuji, Takasaki (JP); Minoru Watanabe, Yokohama (JP); Keigo Yokoyama, Honjo (JP); Jun Kawanabe, Kawasaki (JP); Kazuya Furumoto, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 370 days.

(21) Appl. No.: 15/341,787

(22) Filed: Nov. 2, 2016

(65) Prior Publication Data

US 2017/0128033 A1    May 11, 2017

(30) Foreign Application Priority Data

Nov. 5, 2015   (JP) .................................. 2015-217746

(51) Int. Cl.
*A61B 6/00* (2006.01)
*H04N 5/32* (2006.01)

(52) U.S. Cl.
CPC .............. *A61B 6/54* (2013.01); *A61B 6/4233* (2013.01); *H04N 5/32* (2013.01)

(58) Field of Classification Search
None
See application file for complete search history.

(56) References Cited

U.S. PATENT DOCUMENTS

2015/0363926 A1* 12/2015 Enomoto ............. A61B 6/4233
                                                382/132

FOREIGN PATENT DOCUMENTS

| JP | 2000-023959 A | 1/2000 |
|---|---|---|
| JP | 2011-139761 A | 7/2011 |
| JP | 2013-135390 A | 7/2013 |
| JP | 2014-219248 A | 11/2014 |

* cited by examiner

*Primary Examiner* — Hoon K Song
(74) *Attorney, Agent, or Firm* — Canon U.S.A., Inc. IP Division

(57) ABSTRACT

An apparatus includes a plurality of detection pixels configured to generate a signal according to a radiation irradiation amount to obtain radiation irradiation information, a detection unit configured to correspond to a region of the plurality of detection pixels and detect one of light, pressure, capacitance, and temperature as two-dimensional information, and a control unit configured to determine a monitoring target detection pixel and a non-monitoring-target detection pixel among the plurality of detection pixels based on the two-dimensional information detected by the detection unit, read the signals of detection pixels of a row in which the monitoring target detection pixel is included.

20 Claims, 18 Drawing Sheets

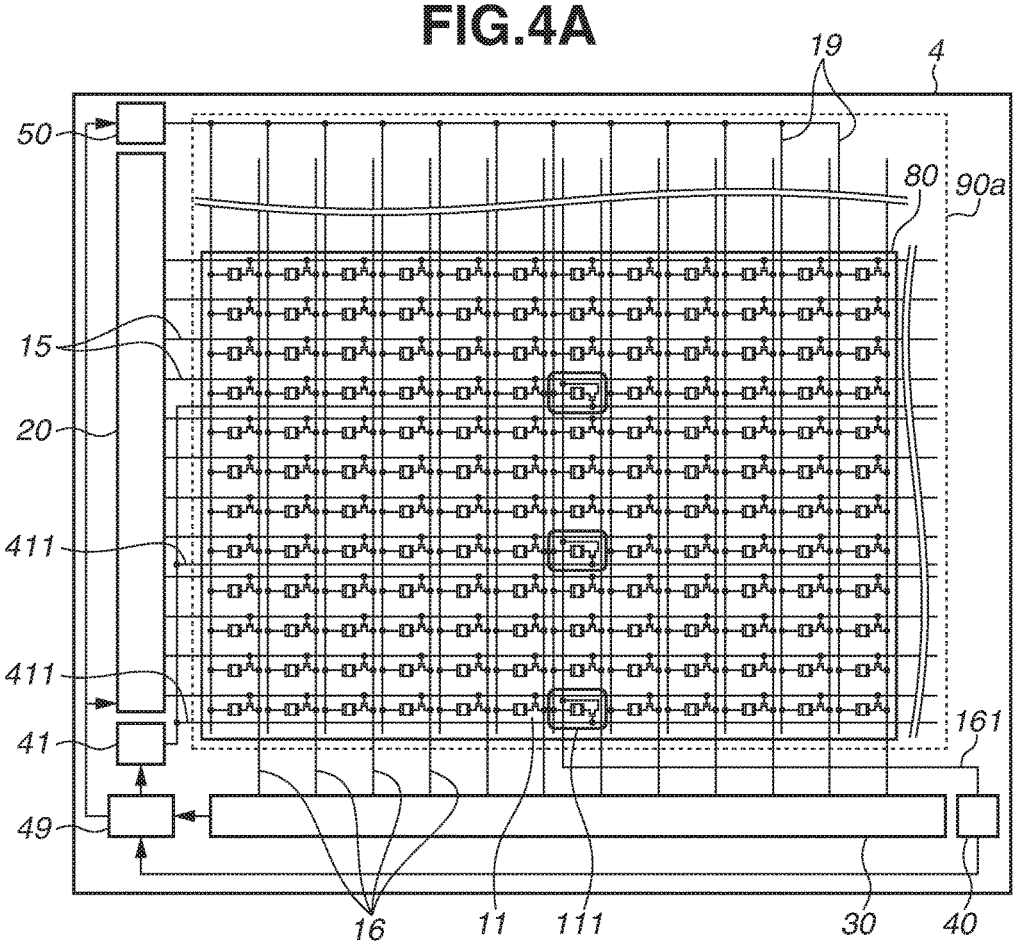
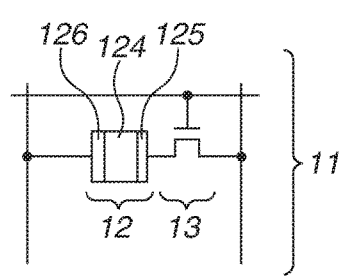 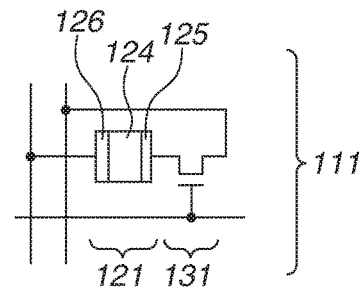

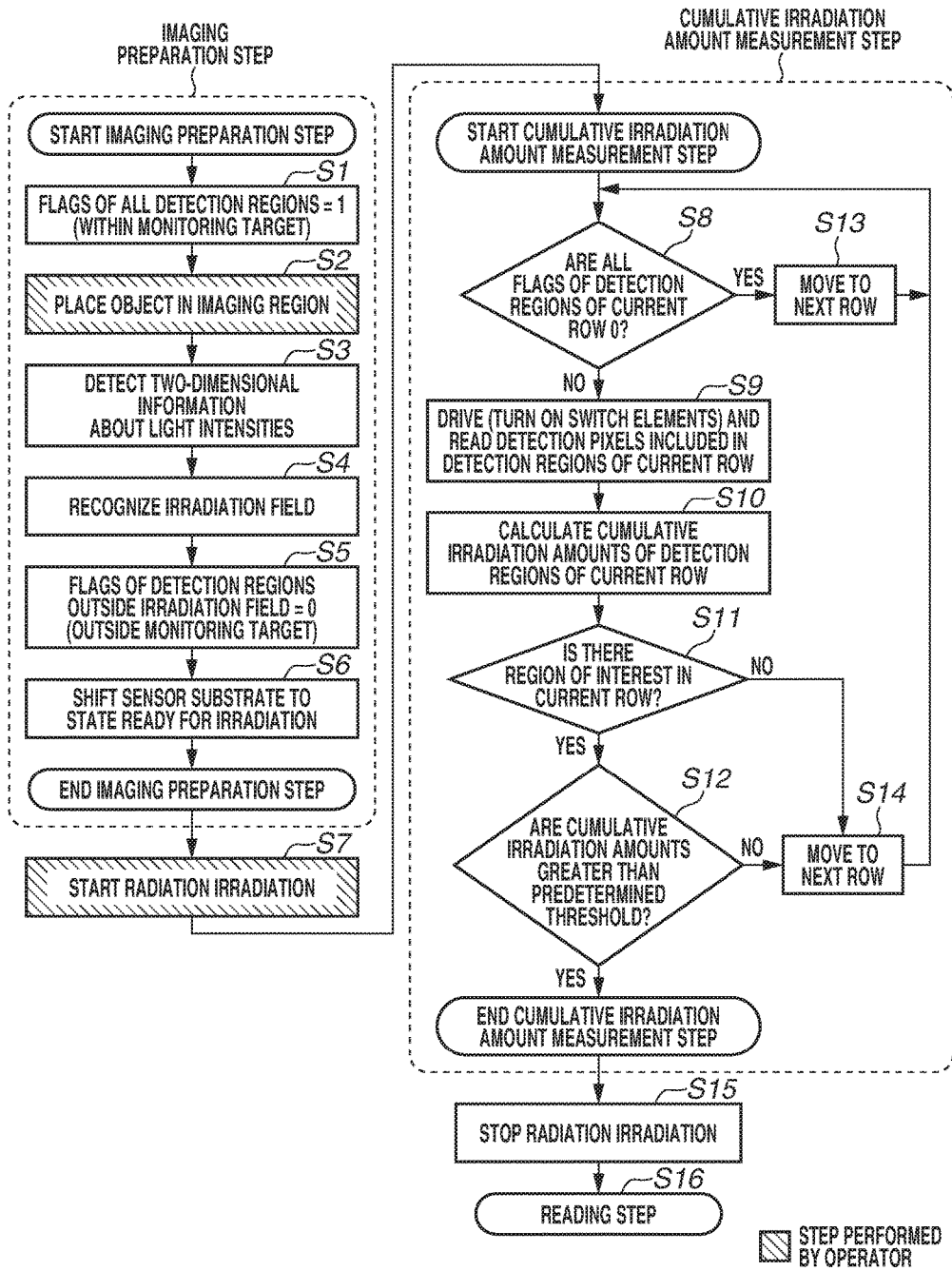

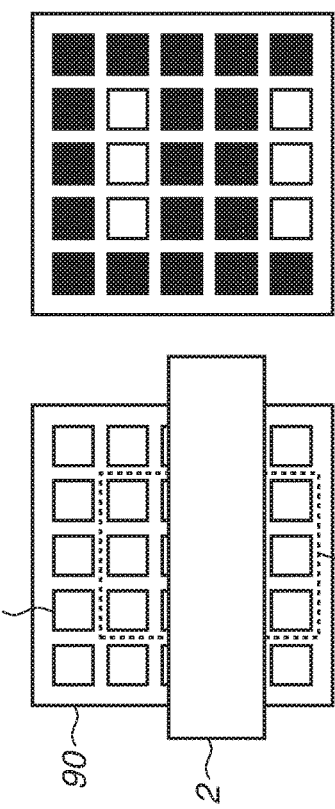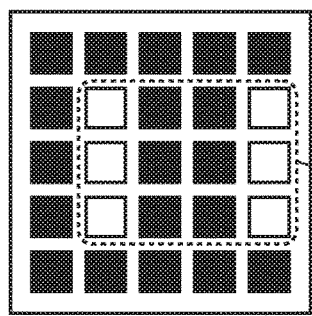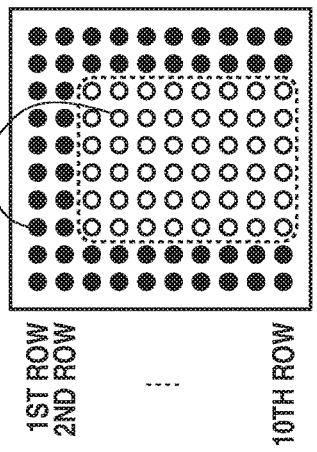

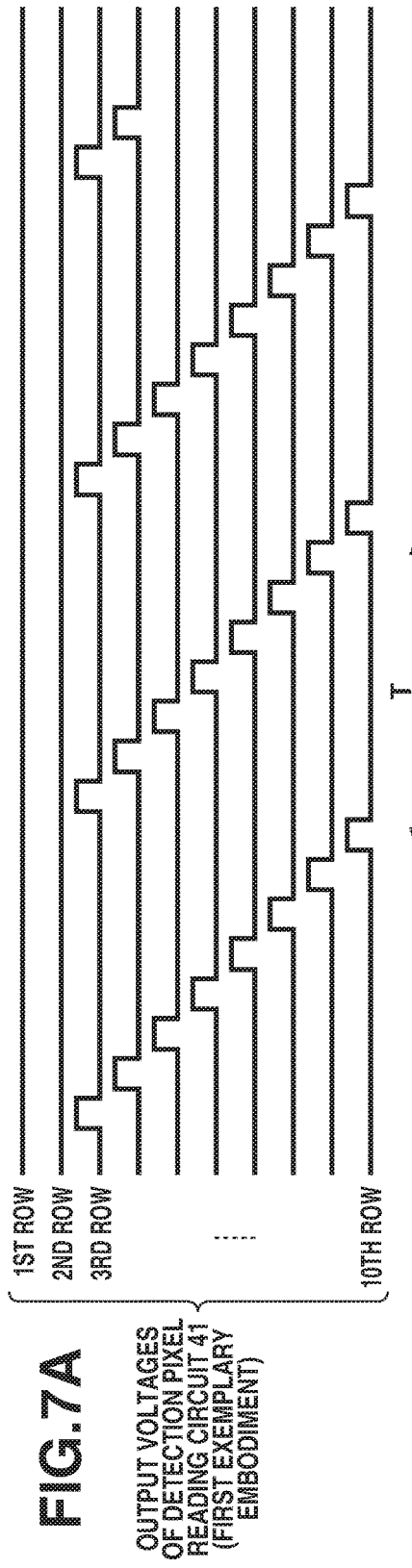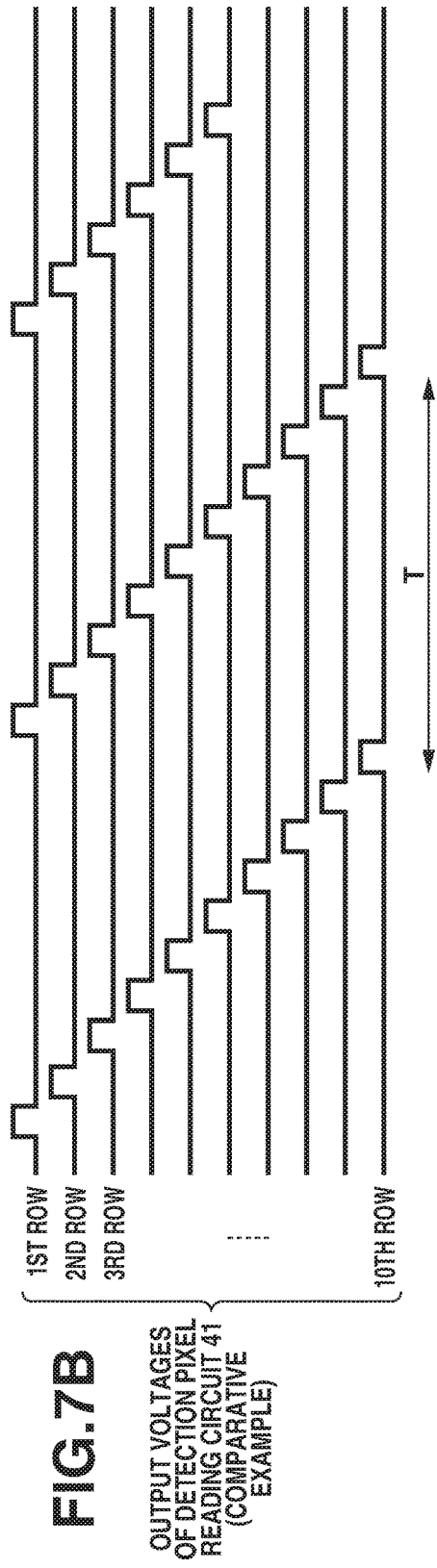

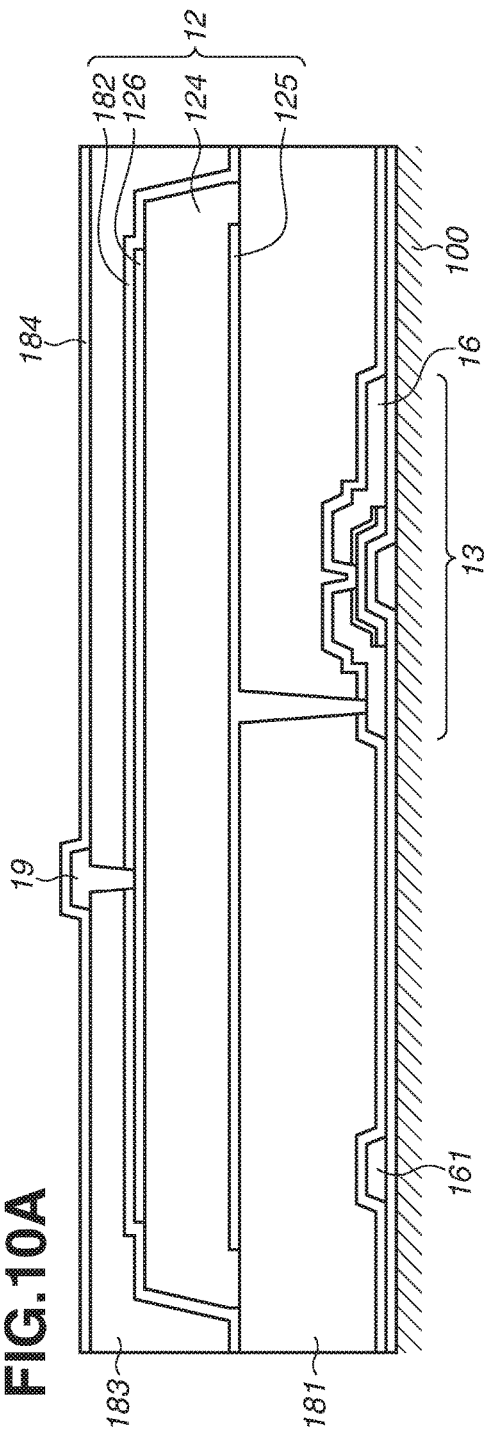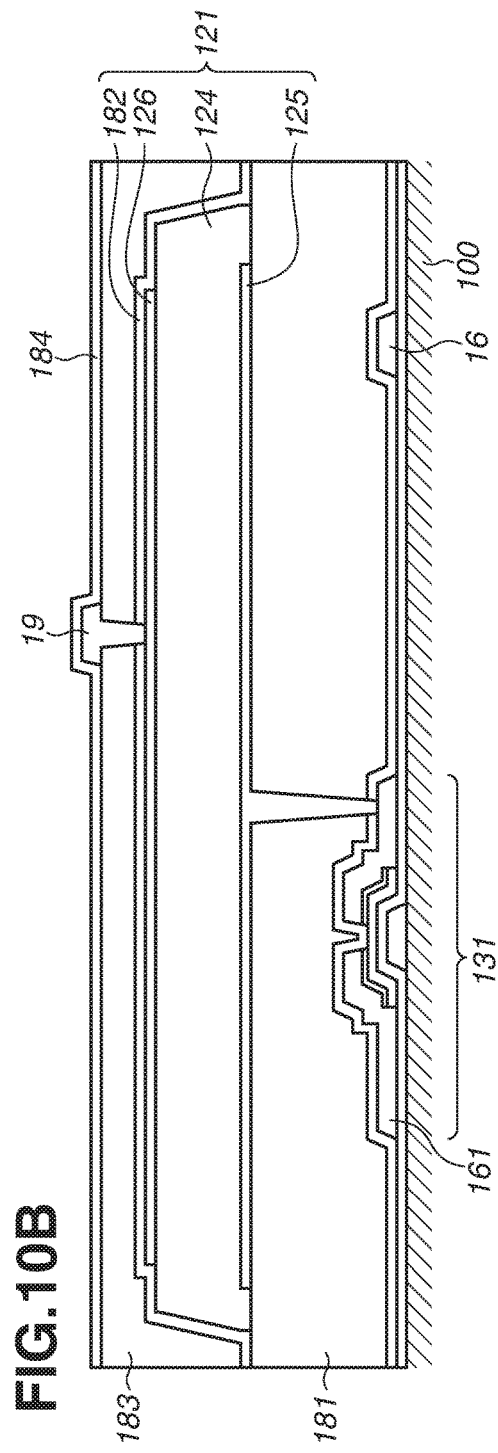

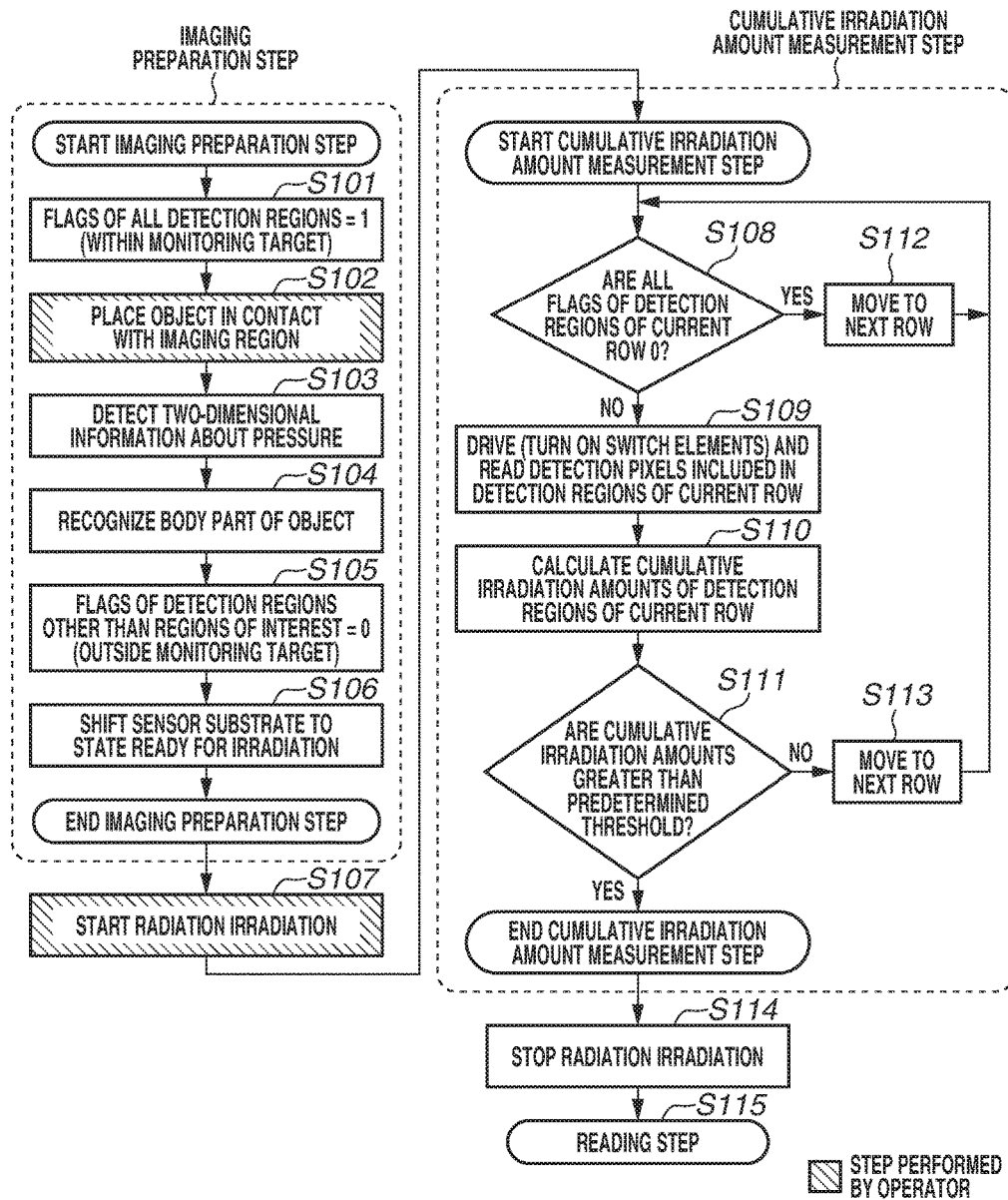

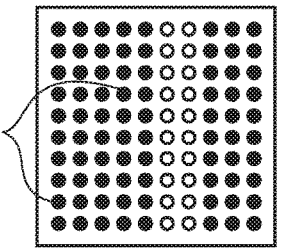
FIG. 13A
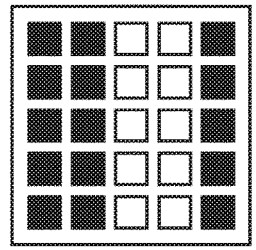
FIG. 13B
LIMB
FIG. 13C
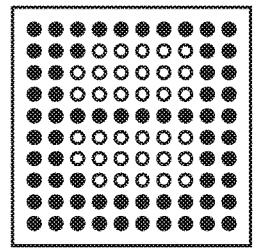
FIG. 13D
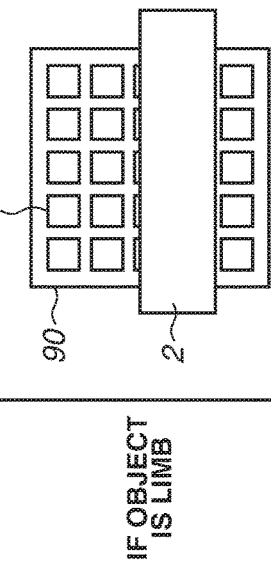
FIG. 13E
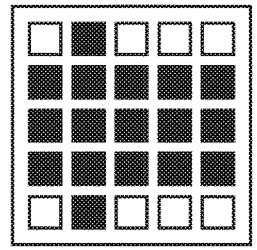
FIG. 13F
CHEST
FIG. 13G
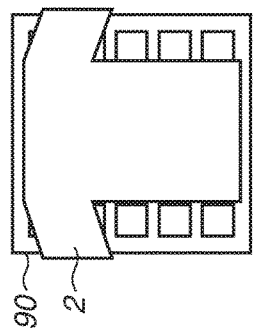
FIG. 13H

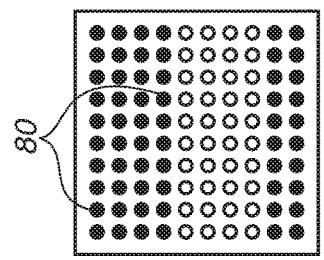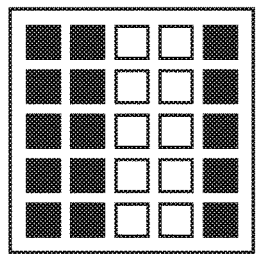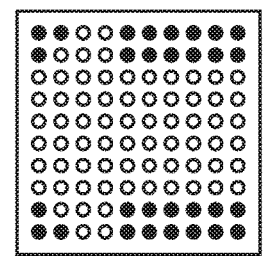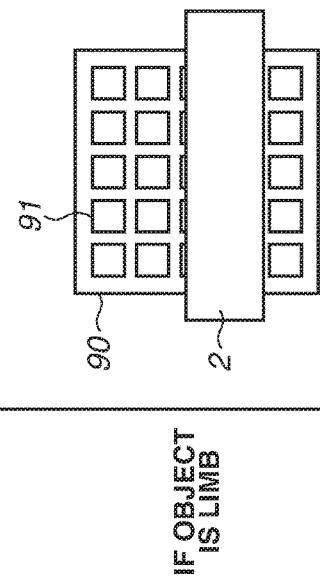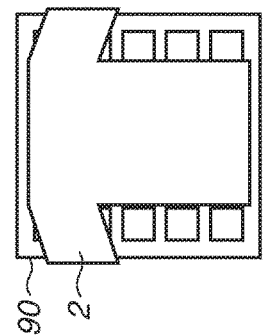

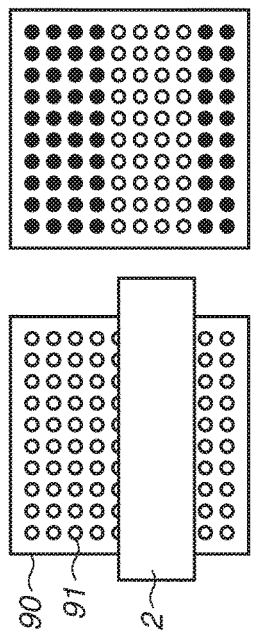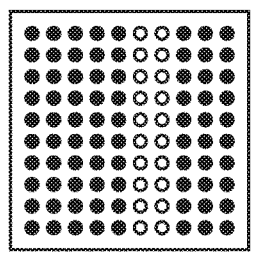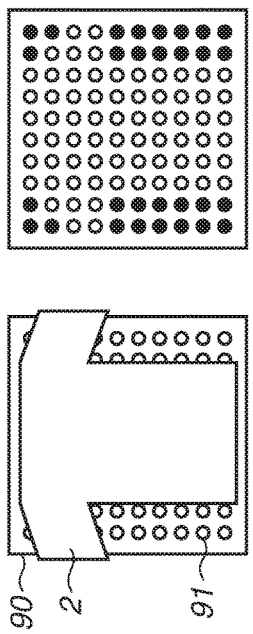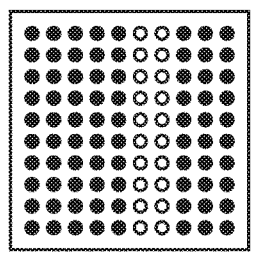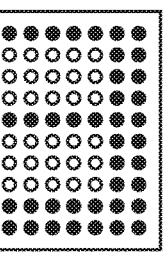

RADIATION DETECTION APPARATUS, RADIATION DETECTION SYSTEM, AND METHOD FOR CONTROLLING RADIATION DETECTION APPARATUS

BACKGROUND OF THE INVENTION

Field of the Invention

The aspect of the embodiments relates to a radiation detection apparatus, a radiation detection system, and a method for controlling a radiation detection apparatus.

Description of the Related Art

An apparatus includes a plurality of pixels, a scanning circuit, and a reading circuit. Each pixel includes a conversion element for converting radiations into an electric charge, and a switch element such as a thin-film transistor. As part of multi-functionalization, an automatic exposure control (AEC) function has been recently studied to build it into the radiation detection apparatus. With use of such function, the radiation detection apparatus can monitor a cumulative radiation irradiation amount, determine that the cumulative irradiation amount reaches an appropriate amount, and control a radiation source to end the irradiation. Operations such as the monitoring, determination, and control of the cumulative radiation irradiation amount (AEC operation) can be performed so that a region important for image diagnosis is rendered with a dynamic range. Examples of the diagnostically important region include a lung field in chest radiography and a bony part in limb bone imaging. For such purposes, a part or a plurality of regions in an imaging region of the radiation detection apparatus corresponding to such important regions is selected, as regions of interest and subject them to the monitoring and determination of the cumulative irradiation amount.

Japanese Patent Application Laid-Open No. 2013-135390 discusses a radiation image detection apparatus which uses a sensor substrate including pixels for obtaining a diagnostic image and a plurality of pixels for obtaining irradiation information. The radiation image detection apparatus can perform an appropriate AEC operation by dividing the detection pixels into monitoring target detection pixels and other detection pixels based on signal amounts of the respective pixels. Specifically, regions (non-irradiated field) not irradiated with the radiations and regions (through areas) of the radiation image detection apparatus on which the radiations are directly incident without passing through an object, are excluded from monitoring targets.

Japanese Patent Application Laid-Open No. 2013-135390 has the following three issues. A first issue is that the detection pixels located in other than the regions of interest are similarly read as the monitoring target detection pixels. Such a needless operation causes a lack of temporal resolution. A second issue is that a detection pixel which is suitable for an AEC determination is not determined until the irradiation of radiations is carried out. The determination may therefore be made based on an irradiation amount that includes information about regions other than the regions of interest. A third issue is a lack of spatial resolution due to the same cause as that of the second issue.

SUMMARY OF THE INVENTION

According to an aspect of the embodiments, an apparatus includes a plurality of detection pixels configured to generate a signal according to a radiation irradiation amount to obtain radiation irradiation information, a detection unit configured to correspond to a region of the plurality of detection pixels and detect one of light, pressure, capacitance, and temperature as two-dimensional information, and a control unit configured to determine a monitoring target detection pixel and a non-monitoring-target detection pixel among the plurality of detection pixels based on the two-dimensional information detected by the detection unit, read the signals of detection pixels of a row in which the monitoring target detection pixel is included.

Further features of the aspect of the embodiment will become apparent from the following description of exemplary embodiments with reference to the attached drawings.

BRIEF DESCRIPTION OF THE DRAWINGS

FIGS. 4A, 4B, and 4C are circuit diagrams in the vicinity of a detection region.

FIG. 5 is a flowchart illustrating a method for controlling the radiation detection apparatus.

FIGS. 6A, 6B, 6C, and 6D are diagrams illustrating a positional relationship between the radiation detection apparatus and an object.

FIGS. 7A and 7B are timing charts illustrating voltage outputs of a detection pixel scanning circuit.

FIGS. 10A and 10B are sectional views illustrating the layout of the sensor substrate.

FIG. 12 is a flowchart illustrating a method for controlling a radiation detection apparatus.

FIGS. 13A to 13H are diagrams illustrating a positional relationship between the radiation detection apparatus and an object.

FIGS. 15A to 15F are diagrams illustrating a positional relationship between the radiation detection apparatus and an object.

FIGS. 17A to 17H are diagrams illustrating a positional relationship between the radiation detection apparatus and an object.

DESCRIPTION OF THE EMBODIMENTS

Figure 1:
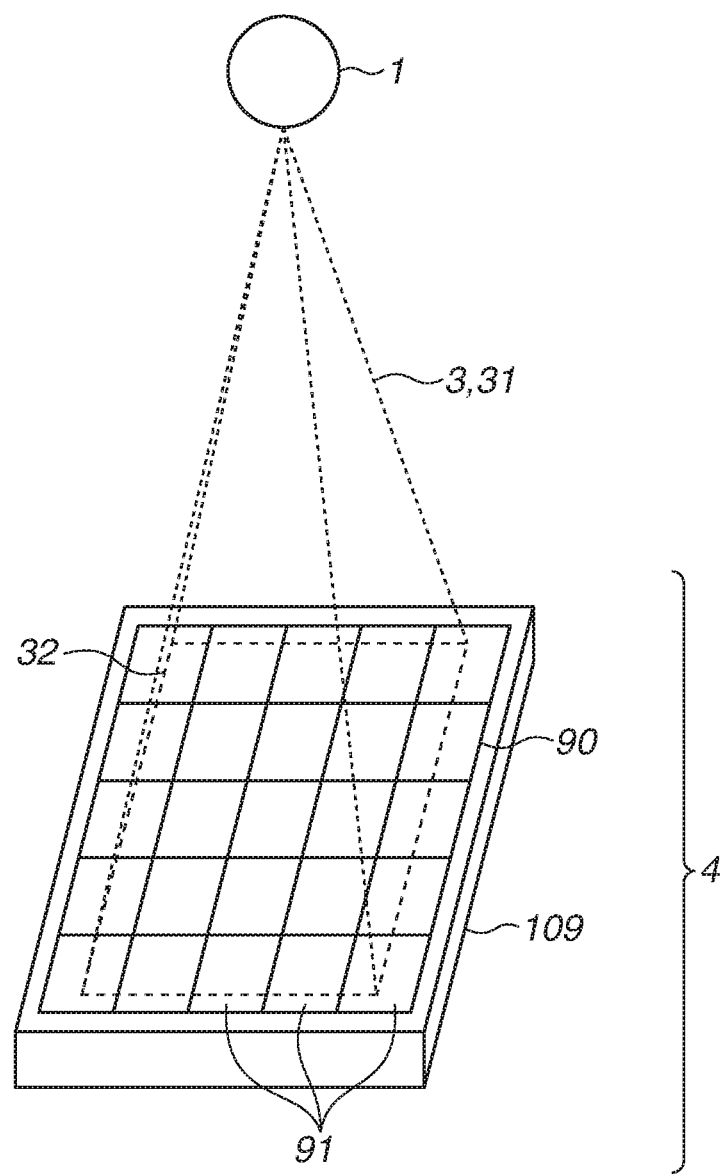
FIG. 1 is a diagram illustrating a configuration example of a radiation detection system.

FIG. 1 is a diagram illustrating a configuration example of a radiation detection system according to a first exemplary embodiment of the aspect of the present invention. The radiation detection system includes a radiation source 1 and a radiation detection apparatus 4. The radiation source 1 emits radiations 3 toward the radiation detection apparatus 4. An example of the radiations 3 is X-rays. In FIG. 1, an object 2 (FIG. 6A) located between the radiation source 1 and the radiation detection apparatus 4 is omitted. The radiation detection apparatus 4 includes a plurality of detection units 91 within an imaging region 90 which is provided on top of a housing 109. The plurality of detection units 91 has the same rectangular shape, and is arranged in a region in which the imaging region 90 is divided into a 5×5 matrix. The shape of the detection units 91, the number of arranged detection units 91, and the method of arrangement are not limited thereto. An irradiation field 32 is the area where the imaging region 90 is irradiated with the radiations 3. In the present exemplary embodiment, the radiation source 1 can irradiate the imaging region 90 with light 31 to illuminate the irradiation field 32. The light 31 is, for example, visible light or infrared rays. However, for the purpose of visually checking the irradiation field 32, the light 31 is to be visible light. The detection units 91 are sensors for detecting the light 31. For example, the detection units 91 are visible light sensors obtained by forming semiconductor thin films and electrodes on a substrate to form photodiodes and applying an appropriate reverse bias to the photodiodes for depletion. The substrate may be made of a resin or glass. The electrodes may be made of metal or a conductive oxide such as indium-tin oxide (ITO). The semiconductor thin films may have a p/n sequential lamination structure using organic or inorganic semiconductor materials, or a bulk hetero-junction structure. Depending on the selected semiconductor thin films, the detection units 91 can be manufactured by using such processes as vacuum deposition and printing.

Figure 2A:
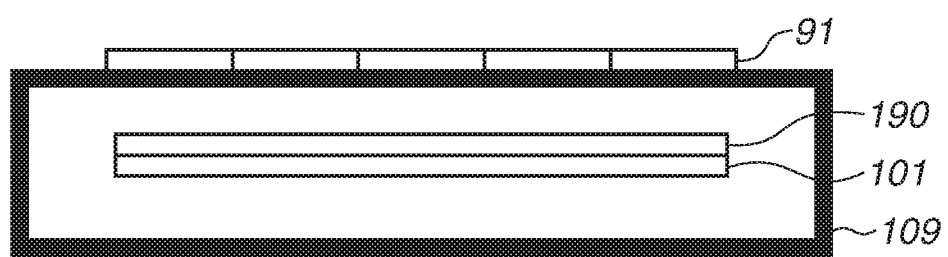
FIGS. 2A and 2B are sectional views illustrating configuration examples of a radiation detection apparatus.
Figure 2B:
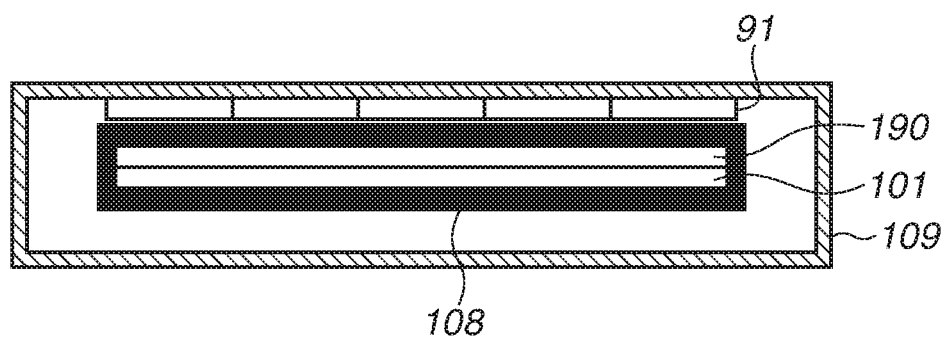

FIGS. 2A and 2B are diagrams illustrating two types of configuration examples of the radiation detection apparatus 4. In FIGS. 2A and 2B, wiring used for the detection units 91 to apply bias and output a signal is omitted. The radiation detection apparatus 4 illustrated in FIG. 2A will initially be described. Suppose that the housing 109 transmits radiations but no visible light. The detection units 91 are arranged on the surface of the housing 109. A sensor substrate 101 and a scintillator 190 are arranged in the housing 109 to be opposed to each other. The scintillator 190 converts the radiations incident on the radiation detection apparatus 4 into visible light. The sensor substrate 101 converts the visible light converted by the scintillator 190 into charges to generate a two-dimensional image. Since radiations are incident on the radiation detection apparatus 4 according to transmittance of radiation through the object 2, the sensor substrate 101 generates a two-dimensional image according to the radiation transmittance through the object 2. If visible light passes through the housing 109, the detection units 91 may be arranged inside the housing 109 as illustrated in FIG. 2B. In such a case, the sensor substrate 101 and the scintillator 190 are to be covered with a light shielding member 108.

Figure 3:
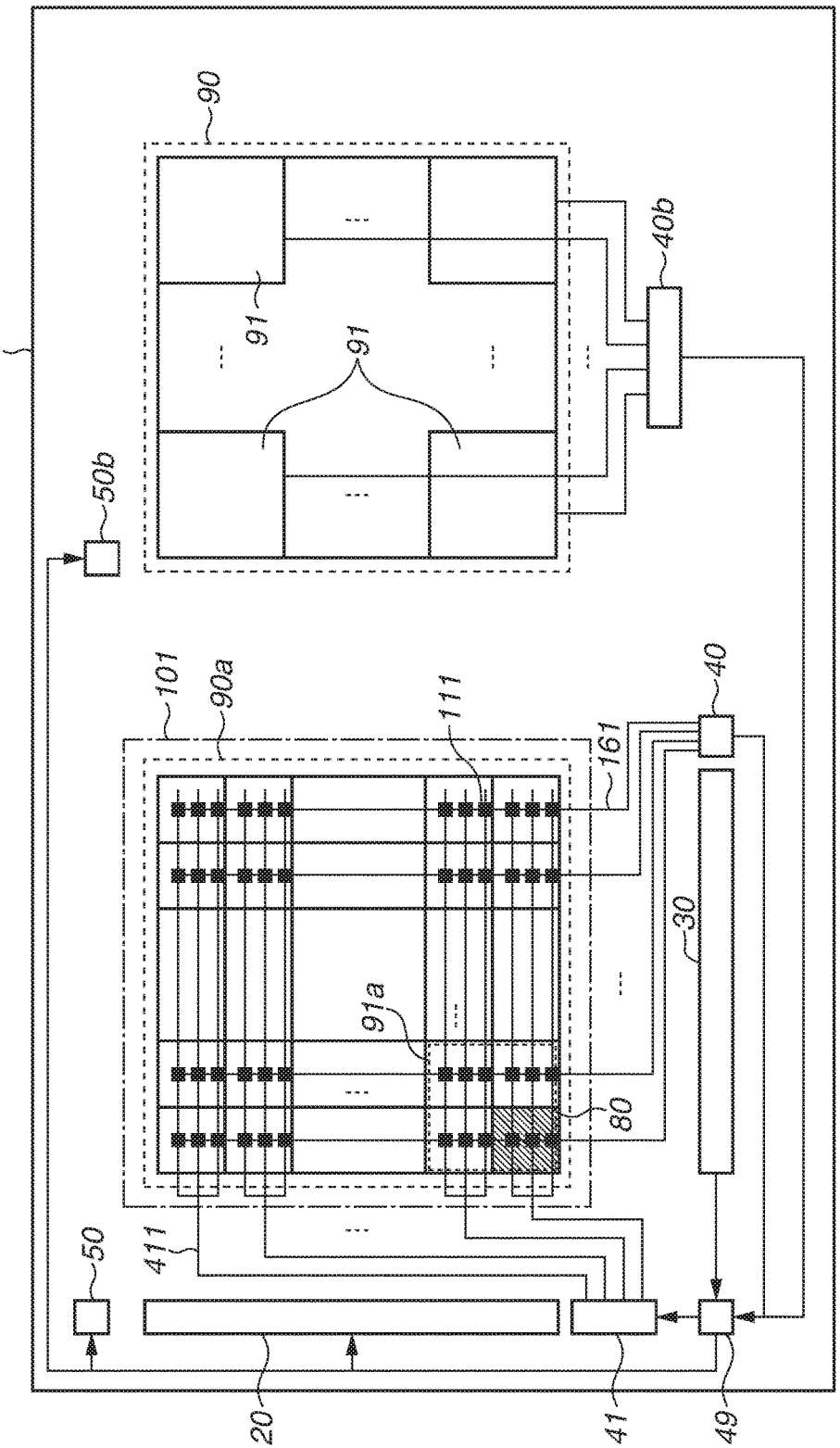
FIG. 3 is a diagram illustrating a configuration example of the radiation detection apparatus.

FIG. 3 is a diagram illustrating a configuration example of the radiation detection apparatus 4. For the sake of viewability, FIG. 3 illustrates the sensor substrate 101 and the detection units 91 next to each other. In fact, the sensor substrate 101 and the detection units 91 are arranged to overlap each other in the housing 109 as illustrated in FIG. 2B. A region of the sensor substrate 101 corresponding to the imaging region 90 will be referred to as an imaging region 90a. A region corresponding to a detection unit 91 will be referred to as a region 91a. As illustrated in FIG. 4A, the imaging region 90a includes detection pixels 111 and normal pixels 11 which are arranged in a matrix. The plurality of detection pixels 111 is arranged in the region of the plurality of normal pixels 11. In FIG. 3, the normal pixels 11 are omitted. The normal pixels 11 and the detection pixels 111 convert visible light converted by the scintillator 190 into electric charges. In other words, the normal pixels 11 and the detection pixels 111 generate electric charges (signals) according to a radiation irradiation amount. The normal pixels 11 and the detection pixels 111 will hereinafter be referred to collectively as pixels. The imaging region 90a includes approximately 1000×1000 to 3000×3000 pixels. The normal pixels 11 are arranged in a two-dimensional matrix over the entire imaging region 90a to generate a two-dimensional image for diagnostic use. The imaging region 90a includes 100 detection regions 80 which are arranged in a two-dimensional matrix with ten rows and ten columns. FIG. 3 illustrates one of detection regions 80 with oblique lines. The detection pixels 111 are provided in each detection region 80 to obtain radiation irradiation information such as a start of irradiation and a cumulative irradiation amount. A plurality of detection pixels 111 may be provided in each detection region 80. In FIG. 3, each pixel detection region 80 includes three detection pixels 111. The detection pixels 111 of detection regions 80 located on the same column are all connected to a common detection line. A control unit 49 controls a scanning circuit 20, a reading circuit 30, a detection pixel scanning circuit 41, a detection pixel reading circuit 40, and a bias power supply 50 to perform various operations. The control unit 49 can select one or more of the plurality of detection regions 80 and obtain irradiation information about each of the detection regions 80. The control unit 49 can temporarily store the irradiation information and calculate a cumulative irradiation amount. The control unit 49 may be connected to the radiation source 1 in a wired or wireless manner, and input a start signal and a stop signal of the radiation source 1 and output an irradiation stop signal to the radiation source 1. The imaging region 90a includes a plurality of detection pixel control lines 411 for driving the detection pixels 111. The detection pixel scanning circuit 41 sequentially drives the plurality of detection pixel control lines 411. As illustrated in FIG. 3, the detection pixel control lines 411 may be branched so that one output terminal of the detection pixel scanning circuit simultaneously drives a plurality of detection pixels 111.

As described above, the detection units 91 are arranged in the respective regions into which the imaging region 90 is divided in a 5×5 matrix. The regions of the detection units 91 correspond to the regions 91a on the sensor substrate 101. The regions 91a each include four detection regions 80. In other words, four detection regions 80 correspond to one detection unit 91. A bias power supply 50b applies a bias voltage to the detection units 91. A reading circuit 40b reads the signals of the detection units 91. The control unit 49 controls the bias power supply 50b and the reading circuit 40b. The following items which have been described above are just an example. They may be differently defined from the foregoing description:

The numbers of pixels, detection regions 80, and detection units 91

The number and positions of detection pixels 111 in each detection region 80

The number and positions of detection regions 80 corresponding to a detection unit 91

The numbers of various lines

FIG. 4A is an enlarged view of circuits in the vicinity of the detection region 80 illustrated by hatching in FIG. 3. The detection region 80 includes a plurality of pixels (three detection pixels 111 and other normal pixels 11) arranged in a matrix. As illustrated in FIG. 4B, the normal pixels 11 each include a conversion element 12 and a switch element 13. The conversion element 12 includes a photodiode 124, a first electrode 125, and a second electrode 126, and converts light into an electric charge. The first electrode 125 of the conversion element 12 is electrically connected to a drain electrode of the switch element 13. The second electrode 126 of the conversion element 12 is connected to the bias power supply 50 through a bias line 19, whereby a voltage for the conversion element 12 to perform a photoelectric conversion operation is applied. A plurality of signal lines 16 is provided in the column direction. The signal lines 16 are connected to source electrodes of the switch elements 13 of the normal pixels 11 in the respective columns in common. A plurality of control lines 15 is provided in the row direction. The control lines 15 are connected in common to gate electrodes of the switch elements 13 of the normal pixels 11 in each row. The scanning circuit 20 controls the voltage of the control line 15 of each row. The reading circuit 30 reads the signals of the normal pixels 11 via the signal lines 16. If the switch element 13 enters a conducting state, the signal of the conversion element 12 is output to the reading circuit 20 through the signal line 16. The detection pixels 111 each include a conversion element 121 and a switch element 131. Like the conversion element 12, the conversion element 121 includes a photodiode 124, a first electrode 125, and a second electrode 126, and converts light into an electric charge. The first electrode 125 of the conversion element 121 is connected to the drain electrode of the switch element 131. The second electrode 126 of the conversion element 121 is connected to the bias power supply 50 via the bias line 19, whereby a voltage for the conversion element 121 to perform a photoelectric conversion operation is applied. A detection line 161 is connected in common to the source electrodes of the switch elements 131 of the detection pixels 111. A detection pixel control line 411 is connected in common to the gate electrodes of the switch circuits 131 of the detection pixels 111. The detection pixel scanning circuit 41 controls the voltage of the detection pixel control line 411. The detection pixel reading circuit 40 reads the signals of the detection pixels 111 via the detection line 161. If the switch element 131 enters a conducting state, the signal of the conversion element 121 is output to the detection pixel reading circuit 40 via the detection line 161. The plurality of detection pixels 111 includes a plurality of switch elements 131 for reading the signals of the respective detection pixels 111.

Figure 9:
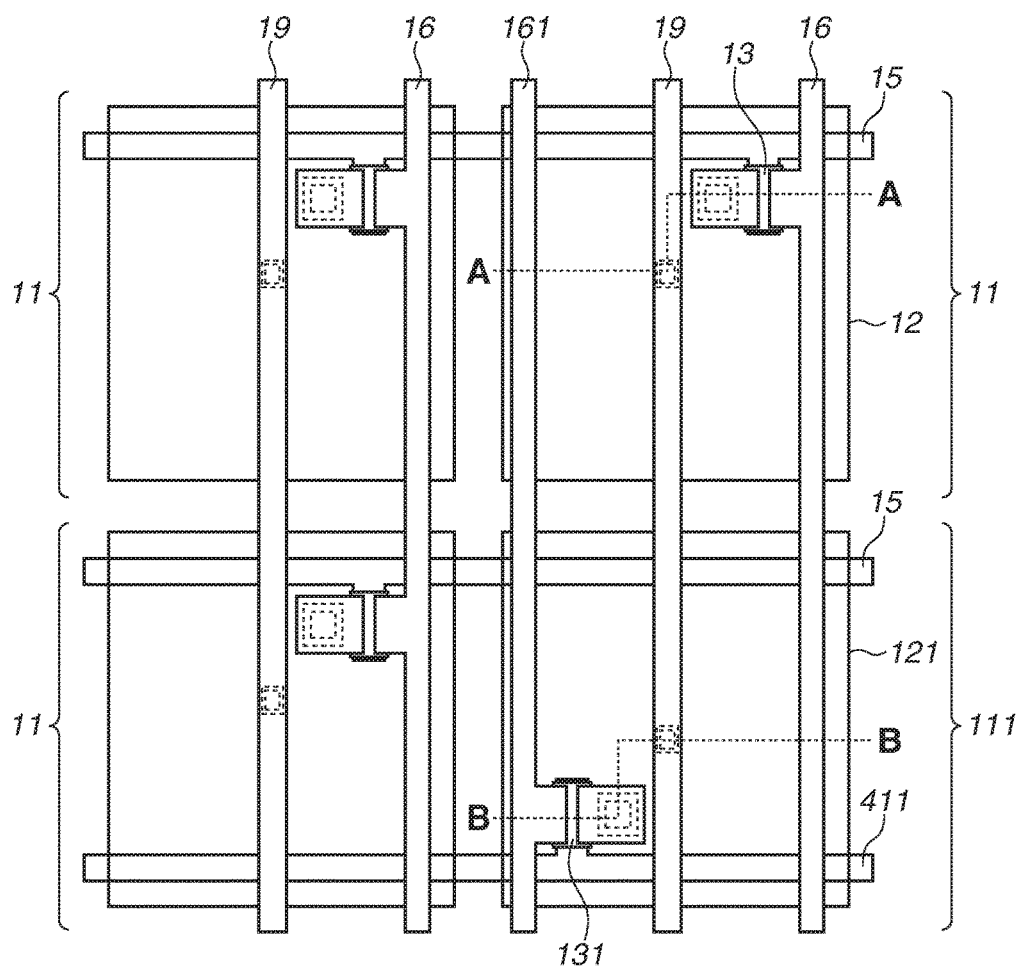
FIG. 9 is a plan view illustrating a layout of a sensor substrate.
Figure 11:
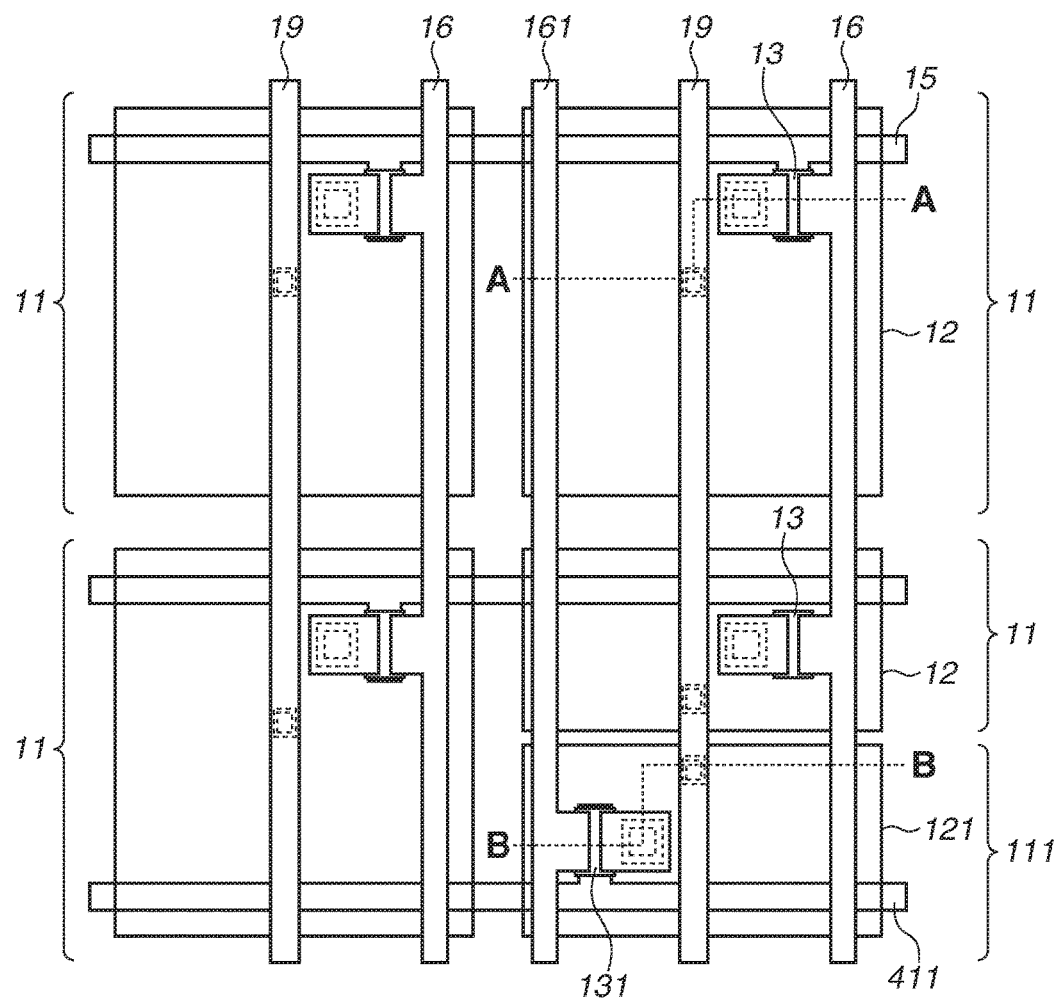
FIG. 11 is a sectional view illustrating the layout of a sensor substrate.

Next, an example of a structure of the normal pixels 11 and the detection pixels 111 used in the sensor substrate 101 will be described. FIG. 9 is a plan view illustrating a layout example of a part of FIG. 4A, in which three normal pixels 11 and one detection pixel 111 are arranged. FIG. 10A is a sectional view of a normal pixel 11 of FIG. 9, taken along the line A-A. FIG. 10B is a sectional view of the detection pixel 111 of FIG. 9, taken along the line B-B. The normal pixel 11 includes the conversion element 12 which converts light into an electric charge, and the switch element 13 which is a thin-film transistor (TFT) for outputting an electrical signal according to the electric charge of the conversion element 12. The conversion element 12 is stacked on the switch element 13 arranged on a substrate 100, with an interlayer insulation layer 181 therebetween. The conversion element 12 is connected to the signal line 16 via the switch element 13. The conversion element 12 includes the first electrode 125, a p-intrinsic-n (PIN) photodiode 124, and the second electrode 126. A protection film 182, a second interlayer insulation layer 183, a common electrode which is integral with the bias line 19, and a protection film 184 are arranged in order on the conversion element 12. A not-illustrated planarization film and the scintillator 190 are arranged on the protection film 184. The second electrode 126 is connected to the bias line 19 via a contact hole. The second electrode 126 is made of optically transparent ITO, and light converted from radiations by the scintillator 190 can pass through the second electrode 126. Like the normal pixel 11, the detection pixel 111 includes the conversion element 121 and the switch element 131. Unlike the normal pixel 11, the conversion element 121 of the detection pixel 111 is connected to the detection line 161 via the switch element 131. The rest of the configuration of the switch element 131 and the conversion element 121 is similar to that of the switch element 13 and the conversion element 12 of the normal pixel 11. In the foregoing description, the conversion elements 12 and 121 are configured to use the PIN photodiode 124. However, the present exemplary embodiment is not limited thereto. For example, metal-insulator-semiconductor (MIS) sensors may be used for the conversion elements 12 and 121. Further, in the foregoing example of FIG. 9, there is no normal pixel 11 in the position corresponding to the detection pixel 111, so that pixel information is missing on the diagnostic image. To avoid this, as illustrated in FIG. 11, the lower right pixel region may be divided into two such that normal pixel 11 and a detection pixel 111 may be juxtaposed in the lower right pixel regions to prevent lacking of pixel information.

FIG. 5 is a flowchart illustrating a method for controlling the radiation detection apparatus 4. The control unit 49 performs the following three operations. In a first operation, the control unit 49 recognizes the irradiation field 32 by using the detection units 91 before irradiating with the radiation. In a second operation, the control unit 49 divides the plurality of detection regions 80 between monitoring target regions inside the irradiation field 32 and monitoring non-target regions outside the irradiation field 32 based on the result of the first operation before irradiating with the radiation. In a third operation, the control unit 49 omits a reading step for the non-monitoring-target regions during the irradiation. Concerning the foregoing procedure, a flow of steps performed in the radiation detection apparatus 4 by an operator before radiation imaging will be described with reference to the flowchart of FIG. 5. FIG. 6A illustrates an object 2 which is a limb, for example.

Figure 8A:
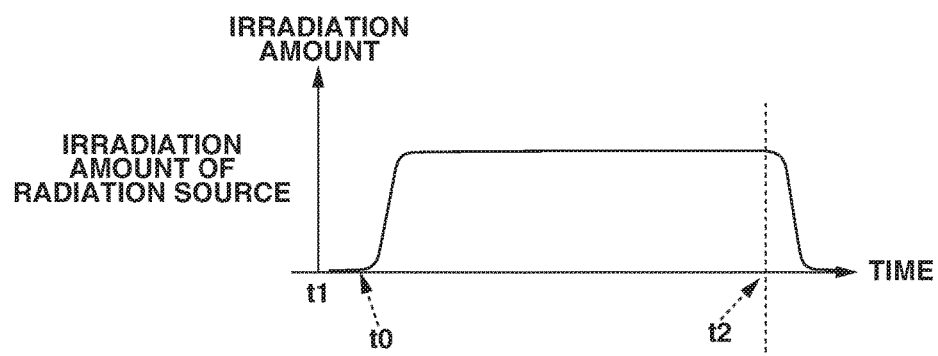
FIGS. 8A, 8B, and 8C are diagrams illustrating a sampling period of a cumulative irradiation amount.

Steps S1 to S6 are an imaging preparation step before the radiation irradiation. The control unit 49 of the radiation detection apparatus 4 has flags for determining whether the respective detection regions 80 are a monitoring target. In step S1, the control unit 49 initializes all the flags to one (within a monitoring target) to treat all the detection regions 80 as a monitoring target. In step S2, as illustrated in FIG. 6A, the operator places the object 2 in the imaging region 90 and positions the radiation source 1. At this time, the operator irradiates the imaging region 90 with the visible light 31 from the radiation source 1, and checks the position of the irradiation field 32. In step S3, the control unit 49 reads two-dimensional information about light intensities detected by the detection units 91 to obtain the two-dimensional information about the light intensities illustrated in FIG. 6B. The detection units 91 each output either ON or OFF information to the control unit 49 according to the light intensity. The detection units 91 may output intermediate information between ON and OFF. In step S4, the control unit 49 recognizes the irradiation field 32 illustrated in FIG. 6C based on the two-dimensional information about the light intensities of the detection units 91 (the foregoing first operation). In other words, the detection units 91 detect the irradiation field 32 of radiations. In step S5, as illustrated in FIG. 6D, the control unit 49 takes detection regions 80 outside the irradiation field 32 as non-monitoring-target regions, and sets the flags of the detection regions 80 to 0 (the foregoing second operation). Detection regions 80 within the irradiation field 32 are taken as the monitoring target regions, and the flags of such detection regions 80 are maintained at 1. In other words, the control unit 49 determines monitoring target detection pixels 111 and non-monitoring-target detection pixels 111 among the plurality of detection pixels 111 based on the two-dimensional information detected by the detection units 91. In step S6, the control unit 49 stops an operation for discharging needless dark charges from the pixels (dummy read), and shifts the sensor substrate 101 to a state of irradiation ready. By the processing up to step S6, the radiation detection apparatus 4 becomes ready to be irradiated with radiations. In step S7, after preparation of the radiation detection apparatus 4 is completed, the operator gives an instruction to start irradiating the radiation detection apparatus 4 with the radiations. Thus, as illustrated in FIG. 8A, at time t0, the radiation source 1 starts to irradiate the radiation detection apparatus 4 with the radiations 3.

Steps S8 to S14 are a process for measuring a cumulative irradiation amount during the radiation irradiation. At time t1, the control unit 49 starts measuring the cumulative irradiation amounts. As illustrated in FIG. 8A, the control unit 49 may start measuring the cumulative irradiation amount process of steps S8 to S14 at time t1 immediately after the end of the imaging preparation process of steps S1 to S6, before the irradiation start time t0 of step S7. In steps S8 to S14, the control unit 49 sequentially determines the cumulative irradiation amounts in the respective detection regions 80. In step S8, the control unit 49 determines whether all the flags of the detection regions 80 of the current row are zero. If all the flags are zero (YES in step S8), the processing proceeds to step S13. If not all the flags are zero (NO in step S8), the processing proceeds to step S9. In step S13, the control unit 49 moves to the next row. The processing returns to step S8. In the case of FIG. 6D, the processing proceeds from step S8 to step S13 in the first and second rows because all the flags of the detection regions 80 are zero. In the third and subsequent rows, there are detection regions 80 with a flag of one. The processing thus proceeds from step S8 to step S9. In step S9, the control unit 49 turns on the switch elements 131 of the detection pixels 111 within the detection regions 80 of the current row, so that the signals of the detection pixels 111 in the detection regions 80 of the current row are output to the detection pixel reading circuit 40. In other words, the control unit 49 reads the signals of the detection pixels 111 of the rows in which the monitoring target detection pixels 111 are included, and does not read the signals of the detection pixels 111 of the rows in which no monitoring target detection pixel 111 is included. Specifically, the control unit 49 brings the switch elements 131 of the detection pixels 111 of the rows in which the monitoring target detection pixels 111 are included, into a conducting state on a row-by-row basis, to read the signals of the detection pixels 111 of the rows in which monitoring target detection pixels 111 are included on a row-by-row basis. The control unit 49 maintains the switch elements 31 of the detection pixels 111 of the rows in which no monitoring-target-detection-pixel 111 is included in a non-conducting state. In step S10, the control unit 49 adds up the signals of the detection pixels 111 in the respective detection regions 80 of the current row to calculate the cumulative irradiation amounts of the respective detection regions 80 of the current row since the start of the irradiation. In step S11, the control unit 49 determines whether there is a region of interest among the detection regions 80 of the current row. For example, the control unit 49 may make the determination estimating that a detection region 80 located near a center of the irradiation field 32 is a region of interest. If there is a region of interest among the detection regions 80 of the current row (YES in step S11), the processing proceeds to step S12. If there is no region of interest among the detection regions 80 of the current row (NO in step S11), the processing proceeds to step S14. In step S14, the control unit 49 moves to the next row. The processing returns to step S8. In step S12, the control unit 49 determines whether the cumulative irradiation amounts of the detection regions 80 of the current row are greater than a predetermined threshold (AEC operation). In other words, the control unit 49 determines whether the read row is a row including a region of interest and a cumulative irradiation amount based on the signals of the detection pixels 111 of the read row exceeds the threshold. The threshold is a value input by the operator in advance or a value determined by the control unit 49 based on various determination results. If the cumulative irradiation amounts are smaller than or equal to the threshold (NO in step S12), the processing proceeds to step S14. If the cumulative irradiation amounts are greater than the threshold (YES in step S12), the cumulative radiation irradiation amount measurement step ends. The processing proceeds to step S15.

Figure 8B:
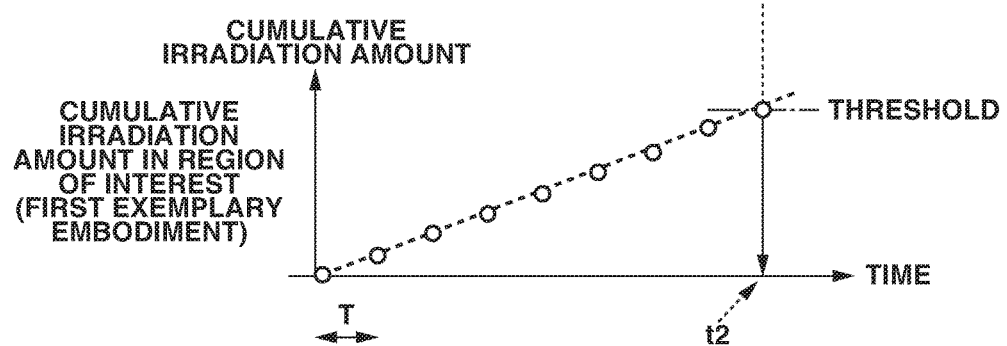

FIG. 7A is a timing chart illustrating voltages of voltage output terminals (first to tenth rows) of the detection pixel scanning circuit 41 in the cumulative irradiation measurement step of steps S8 to S14. In the case of FIG. 6D, the detection pixel scanning circuit 41 successively outputs high level pulses only to the detection regions 80 of the third to tenth rows. In a high-level period of FIG. 7A, the switch elements 131 in the detection regions 80 of the row become conducting, and the signals of the detection pixels 111 in the detection regions 80 of the row are output to the detection pixel reading circuit 40. The detection pixel reading circuit 40 successively receives the signals of the detection pixels 111 in the detection regions 80 of the third to tenth rows. The detection pixel reading circuit 40 sequentially updates the cumulative irradiation amounts of the detection regions 80 of the third to tenth rows at periods T (sampling periods) illustrated in FIGS. 7A and 8B. FIG. 8B illustrates how the cumulative irradiation amount is updated. At time t2, the cumulative irradiation amount of a region of interest among the detection regions 80 of the third to tenth rows exceeds the threshold. The control unit 49 determines that the cumulative irradiation amounts directed to the radiation detection apparatus 4 are optimum, and the cumulative irradiation amount measurement step ends. As described above, the control unit 49 does not read the detection regions 80 of the first or second row which are not a monitoring target (the foregoing third operation). The detection pixel reading circuit 40 may perform other controls. In particular, in step S9 of reading the detection regions 80 of the third to tenth rows, the detection pixel reading circuit 40 can suspend at least a part of the operation to suppress power consumption. A case will be described as an example in which the detection pixel reading circuit 40 includes various circuit blocks such as an integration amplifier, a correlated double sampling (CDS) circuit, and an analog-to-digital (A/D) converter for each detection line 161. In such a case, the detection pixel reading circuit 40 can suspend a part or all of operation of the blocks to reduce power consumption according to the values (1 or 0) of the flags of the detection regions 80 in the third to tenth rows. In other words, the detection pixel reading circuit 40 processes the signals read from the monitoring target detection pixels 111 and suspends the processing of the signals read from the non-monitoring-target detection pixels 111 according to the values of the flags of the detection regions 80 in the third to tenth rows.

In FIG. 5, in step S15, the control unit 49 outputs an irradiation stop signal to the radiation source 1. Consequently, as illustrated in FIG. 8A, the radiation source 1 stops the irradiation of the radiations 3 at time t2. In step S16, the control unit 49 drives the scanning circuit 20 in a line sequential manner to read the signals of the normal pixels 11 of all the rows into the reading circuit 30 in the line sequential manner. The reading circuit 30 forms a diagnostic image based on the signals input from all the normal pixels 11.

Through the foregoing processing, the radiation detection apparatus 4 can measure the cumulative irradiation amounts. The radiation detection apparatus 4 may obtain irradiation amount information other than the cumulative irradiation amounts (such as an instantaneous irradiation amount and a temporal change rate of the irradiation amount) based on irradiation amount signals of the detection pixels 111. When the radiation detection apparatus 4 obtains the cumulative irradiation amounts, instead of adding up the irradiation amount signals to directly determine the cumulative irradiation amounts, the radiation detection apparatus 4 may estimate the information about the cumulative irradiation amounts from the irradiation amount signals at an arbitrary point of time.

Next, effects of the present exemplary embodiment will be described. In the present exemplary embodiment, the plurality of detection units 91 for detecting light is two-dimensionally arranged to correspond to the imaging region 90. Based on the two-dimensional output pattern from the detection units 91, regions of interest are narrowed down in advance before the radiation irradiation. This can save needless operations to increase the temporal resolution. In the present exemplary embodiment, information about regions other than the regions of interest can be excluded to increase the AEC accuracy and the spatial resolution. In the present exemplary embodiment, the sampling period T can be reduced by choosing not to read signals from the detection pixels 111 in the detection regions 80 of the first and second rows which are not a monitoring target. As a result, the temporal resolution of the AEC operation can be increased.

Figure 8C:
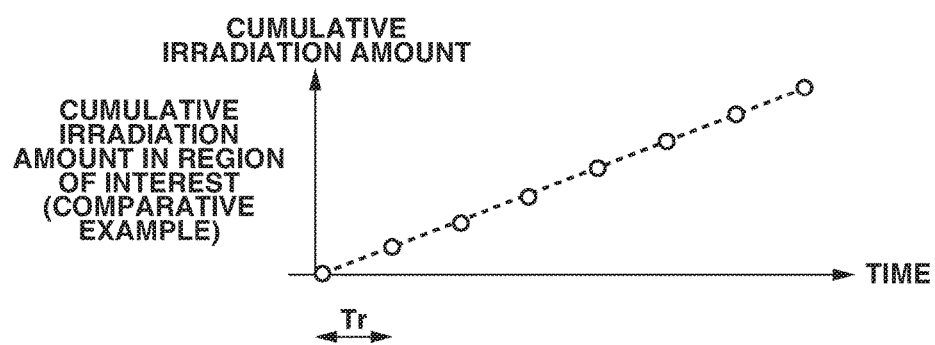

FIGS. 7B and 8C are a timing chart and a diagram illustrating the update timing of the cumulative irradiation amount according to a comparative example, in a case where the reading of the signals are not omitted which are read from the detection pixels 111 in the detection regions 80 of the first and second rows which are not a monitoring target. The sampling period in such a case is Tr. Since the sampling period T according to the present exemplary embodiment in FIGS. 7A and 8B is shorter than the sampling period Tr of FIGS. 7B and 8C, the present exemplary embodiment is superior in the temporal resolution of the AEC operation. The present exemplary embodiment is particularly effective if the proportion of the irradiation field 32 to the imaging region 90 is small. Further, the present exemplary embodiment can reduce power consumption by suspending the operation of at least a part of the detection pixel reading circuit 40.

A radiation detection system according to a second exemplary embodiment of the aspect of the present invention has a configuration similar to that of the radiation detection system according to the first exemplary embodiment. Differences between the present exemplary embodiment and the first exemplary embodiment will be described below. In the present exemplary embodiment, the detection units 91 are pressure sensors. For example, a resistive film touch panel or micro electro mechanical systems (MEMS) may be used. A case will be described below where the detection units 91 are resistive film pressure sensors as an example. A sectional view of the radiation detection apparatus 4 is similar to FIG. 2A. Like the first exemplary embodiment, the detection units 91 are arranged in respective regions into which the imaging region 90 is divided in a 5×5 matrix. The detection units 91 detect pressure and output the detected pressure to the control unit 49. As will be described below, the control unit 49 refers to a database, recognizes a body part of the object 2 based on two-dimensional information about the pressure detected by the detection units 91, and estimates the positions of monitoring target regions.

FIG. 12 is a flowchart illustrating a method for controlling the radiation detection apparatus 4 according to the second exemplary embodiment of the aspect of the present invention. The control unit 49 performs the following three operations. In a first operation, the control unit 49 recognizes regions where the object 2 is located, by using the detection units 91 before radiation irradiation. In a second operation, before the radiation irradiation, the control unit 49 recognizes the body part of the object 2 based on the result of the first operation, and divides the plurality of detection regions 80 between monitoring target regions including a region of interest, and non-monitoring-target regions not including a region of interest. In a third operation, the control unit 49 omits the reading step from the non-monitoring-target regions during the irradiation. With respect to the above method, a flow of steps performed by the radiation detection apparatus 4 and carried out by the operator up to radiation imaging will be described with reference to the flowchart of FIG. 12. FIG. 13A illustrates the object 2 which is a limb, for example.

Steps S101 to S106 are an imaging preparation step for the radiation irradiation. In step S101, the control unit 49 initializes all the flags to one (within a monitoring target) to take all the detection regions 80 as a monitoring target. In step S102, as illustrated in FIG. 13A, the operator brings the object 2 into contact with the imaging region 90 and positions the radiation source 1. Here, the operator does not need to irradiate the imaging region 90 with the visible light 31 from the radiation source 1. In step S103, the control unit 49 reads two-dimensional information about the pressure detected by the detection units 91 to obtain the two-dimensional information about the pressure illustrated in FIG. 13B. In other words, the detection units 91 detect the position of the object 2. Each detection unit 91 outputs either ON or OFF information to the control unit 49 according to the pressure. In step S104, as illustrated in FIG. 13C, the control unit 49 recognizes the body part of the object 2 (the body part of the portion opposed to the imaging region 90) as a limb based on the two-dimensional information about the pressure of the detection units 91 (the foregoing first operation). In step S105, the control unit 49 refers to the database, and sets regions of interest in the positions indicated by the white circles in FIG. 13D, and sets regions other than the regions of interest in the positions indicated by the black circles in FIG. 13D based on the limb which is the recognized body part of the object 2. Specifically, the control unit 49 takes detections regions 80 other than the regions of interest indicated by the black circles in FIG. 13D as non-monitoring-target regions, and sets the flags of those detection regions 80 to 0 (the foregoing second operation). The detection regions 80 within the regions of interest maintain the flags at one as monitoring target regions. In addition to the database, the control unit 49 can use a console for storing imaging conditions and procedures to more accurately determine the regions of interest. In steps S106 and S107, the radiation detection apparatus 4 then performs processing similar to that of steps S6 and S7 in FIG. 5.

Steps S108 to S113 are a step of measuring a cumulative irradiation amount during the radiation irradiation. In steps S108 to S113, the control unit 49 sequentially determines the cumulative irradiation amounts in the respective detection regions 80. In step S108, the control unit 49 determines whether all the flags of the detection regions 80 of the current row are zero. If all the flags are zero (YES in step S108), the processing proceeds to step S112. If not all the flags are zero (NO in step S108), the processing proceeds to step S109. In step S112, the control unit 49 moves to the next row. The processing returns to step S108. In the case of FIG. 13D, the processing proceeds from step S108 to step S112 in the first to fifth rows and the eighth to tenth rows since all the flags of the detection regions 80 are zero. In the sixth and seventh rows, the processing proceeds from step S108 to step S109 since there are detection regions 80 with a flag at one. In step S109, the control unit 49 turns on the switch elements 131 of the detection pixels 111 within the detection regions 80 of the current row to output the signals of the detection pixels 111 in the detection regions 80 of the current row to the detection pixel reading circuit 40. In step S110, the control unit 49 adds up the signals of the detection pixels 111 within the respective detection regions 80 of the current row to calculate the cumulative irradiation amounts of the respective detection regions 80 of the current row since the start of the irradiation. In step S111, the control unit 49 determines whether the cumulative irradiation amounts of the detection regions 80 of the current row are greater than a predetermined threshold (AEC operation). In other words, the control unit 49 determines whether the cumulative irradiation amount based on the signals of the detection pixels 111 in the read row exceeds the threshold. If the cumulative irradiation amounts are smaller than or equal to the threshold (NO in step S111), the processing proceeds to step S113. If the cumulative irradiation amounts are greater than the threshold (YES in step S111), the step of measuring the cumulative irradiation amount ends and the processing proceeds to step S114. In step S113, the control unit 49 moves to the next row. The processing returns to step S108. In step S114, the radiation detection apparatus 4 performs processing similar to that of step S15 in FIG. 5. In step S115, the radiation detection apparatus 4 performs processing similar to that of step S16 in FIG. 5.

FIGS. 13A to 13D described above illustrate the example where the object 2 is a limb. FIGS. 13E to 13H illustrate a case in which the object 2 is the chest. FIGS. 13E to 13H correspond to FIGS. 13A to 13D, respectively. More specifically, FIG. 13F illustrates the reading result of the two-dimensional information about the pressure if the object 2 is the chest illustrated in FIG. 13E. In such a case, the control unit 49 determines that the object 2 is the chest (FIG. 13G) and regions of interest (or candidates thereof) are located in the positions of FIG. 13H corresponding to a lung field in chest imaging.

Next, effects of the present exemplary embodiment will be described. In the present exemplary embodiment, the plurality of detection units 91 for detecting pressure is two-dimensionally arranged to correspond to the imaging region 90. Based on the two-dimensional pressure pattern of the detection units 91, regions of interest are identified in advance before the radiation irradiation. As compared to the first exemplary embodiment, the present exemplary embodiment can more accurately narrow down monitoring target regions, which increases the AEC accuracy.

Aside from the foregoing pressure sensors, for the detection units 91, various sensors that can detect the region of the object 2 may be employed. Specifically, for the detection units 91, the followings can be employed. The detection units 91 may be optical sensors, which detect incident light such as illumination light (ambient light around the radiation detection apparatus 4) in the room in which the object 2 and the radiation detection apparatus 4 are located. The control unit 49 can detect the region of the object 2 by using the detected light like the first exemplary embodiment. Further, the detection units 91 may be capacitance sensors (such as a capacitive touch panel). Furthermore, the detection units 91 may be temperature sensors (such as an organic p-n diode and a pyroelectric element). As described in a fourth exemplary embodiment below, if the electrical characteristics of the normal pixels 11 and the detection pixels 111 have temperature dependence, the detection units 91 may use such characteristics.

A radiation detection system according to a third exemplary embodiment of the aspect of the present invention has a configuration similar to that of the radiation detection system according to the second exemplary embodiment. Differences between the present exemplary embodiment and the second exemplary embodiment will be described below. In the second exemplary embodiment, the regions to which the object 2 is not opposed in the imaging region 90, will not be set as a region of interest. Accordingly, regions of interest do not need to be set by recognizing the body part of the object 2 using the database. In such a case, a portion of the monitoring target regions is to be separately determined as a region of interest. Therefore, the control unit 49 according to the present exemplary embodiment performs the following three operations. In a first operation, the control unit 49 recognizes the region where the object 2 is located, by using the detection units 91 before irradiation is performed. In a second operation, the control unit 49 divides the plurality of detection regions 80 between monitoring target regions where the object 2 is located and non-monitoring-target regions where the object 2 is not located based on the result of the first operation before the irradiation. In a third operation, the control unit 49 omits the step of reading out from the non-monitoring-target regions, during the radiation irradiation. Concerning the foregoing, a flow of steps performed by the radiation detection apparatus 4 and carried out by the operator before radiation imaging is performed will be described with reference to the flowchart of FIG. 14. The object 2 illustrated in FIG. 15A is a limb, for example.

Figure 14:
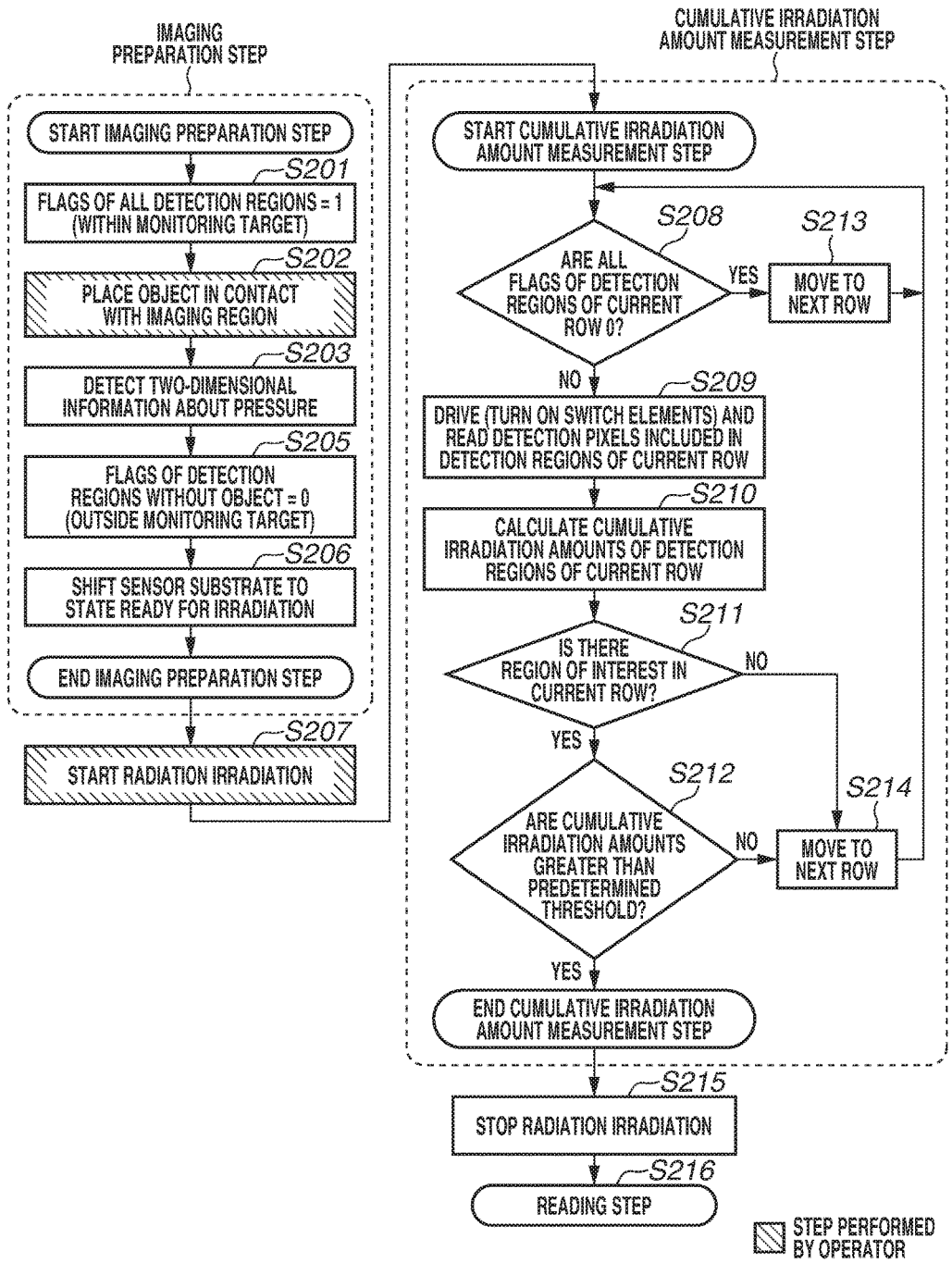
FIG. 14 is a flowchart illustrating a method for controlling a radiation detection apparatus.

FIG. 14 is a flowchart illustrating a method for controlling the radiation detection apparatus 4 according to the third exemplary embodiment of the aspect of the present invention. Steps S201 to S206 are an imaging preparation step before radiation irradiation is performed. In step S201, the control unit 49 performs processing similar to that of step S101 in FIG. 12. In step S202, as illustrated in FIG. 15A, the operator places the object 2 in contact with the imaging region 90 and positions the radiation source 1. In step S203, the control unit 49 reads two-dimensional information about the pressure detected by the detection units 91 to obtain the two-dimensional information about the pressure illustrated in FIG. 15B (the foregoing first operation). In the present exemplary embodiment, step S104 of recognizing the body part of the object 2 in FIG. 12 is not included. In step S205, as illustrated in FIG. 15C, the control unit 49 sets the white-circled detection regions 80 to which the object 2 is opposed, as monitoring target regions, and sets the blackcircled detection regions 80 to which the object 2 is not opposed, as non-monitoring-target regions based on the two-dimensional information about the pressure of the detection units 91. Specifically, the control unit 49 sets the flags of the detection regions 80 that are non-monitoring-target regions indicated by the black circles in FIG. 15C, to zero (the foregoing second operation). The flags of the detection regions that are monitoring target regions are maintained at one. Then, in steps S206 and S207, the radiation detection apparatus 4 performs processing similar to steps S106 and S107 in FIG. 12.

Steps S208 to S214 are a step of measuring cumulative irradiation during the radiation irradiation. In steps S208 to S214, the control unit 49 sequentially determines the cumulative irradiation amounts of the respective detection regions 80. In step S208, the control unit 49 determines whether all the flags of the detection regions 80 of the current row are zero. If all the flags are zero (YES in step S208), the processing proceeds to step S213. If not all the flags are zero (NO in step S208), the processing proceeds to step S209. In step S213, the control unit 49 moves to the next row. The processing returns to step S208. In the case of FIG. 15C, the processing proceeds from step S208 to step S213 in the first to fourth rows and the ninth and tenth rows since all the flags of the detection regions 80 are zero. In the fifth to eighth rows, the processing proceeds from step S208 to step S209 since there are detection regions 80 with a flag at one. In step S209, the control unit 49 turns on the switch elements 131 of the detection pixels 111 within the detection regions 80 of the current row, so that the signals of the detection pixels 111 in the detection regions 80 of the current row are output to the detection pixel reading circuit 40. In step S210, the control unit 49 adds up the signals of the detection pixels 111 within the detection regions 80 of the current row to calculate the cumulative irradiation amounts of the respective detection regions 80 of the current row since the start of the irradiation. In step S211, the control unit 49 determines whether there is a region of interest among the detection regions 80 of the current row. For example, the control unit 49 may make the determination by estimating a detection region 80 located near the center of the irradiation field 32 as a region of interest. If there is a region of interest among the detection regions 80 of the current row (YES in step S211), the processing proceeds to step S212. If there is no region of interest among the detection regions 80 of the current row (NO in step S211), the processing proceeds to step S214. In step S214, the control unit 49 moves to the next row. The processing returns to step S208. In step S212, the control unit 49 determines whether the cumulative irradiation amounts of the detection regions 80 of the current row are greater than a predetermined threshold (AEC operation). If the cumulative radiation irradiation amounts are smaller than or equal to the threshold (NO in step S212), the processing proceeds to step S214. If the cumulative irradiation amounts are greater than the threshold (YES in step S212), the step of measuring the cumulative irradiation amount step ends and the processing proceeds to step S215. In step S215, the radiation detection apparatus 4 performs processing similar to step S114 in FIG. 12. In step S216, the radiation detection apparatus 4 performs processing similar to step S115 in FIG. 12.

FIGS. 15A to 15C described above illustrate the example where the object 2 is a limb. FIGS. 15D to 15F illustrates a case in which the object 2 is the chest. FIGS. 15D to 15F correspond to FIGS. 15A to 15C, respectively. More specifically, FIG. 15E illustrates the reading result of the two-dimensional information about the pressure if the object 2 is the chest illustrated in FIG. 15D. FIG. 15F illustrates the monitoring target regions.

Next, effects of the present exemplary embodiment will be described. In the present exemplary embodiment, the plurality of detection units 91 for detecting pressure is two-dimensionally arranged to correspond to the imaging region 90. Based on the two-dimensional pressure pattern of the detection units 91, regions of interest are narrowed down in advance before the irradiation is performed. According to the present exemplary embodiment, the regions of interest are narrowed down with accuracy lower than in the second exemplary embodiment. However, configuration of the radiation detection apparatus 4 and the radiation detection system can be simplified because the database is not needed.

Figure 16A:
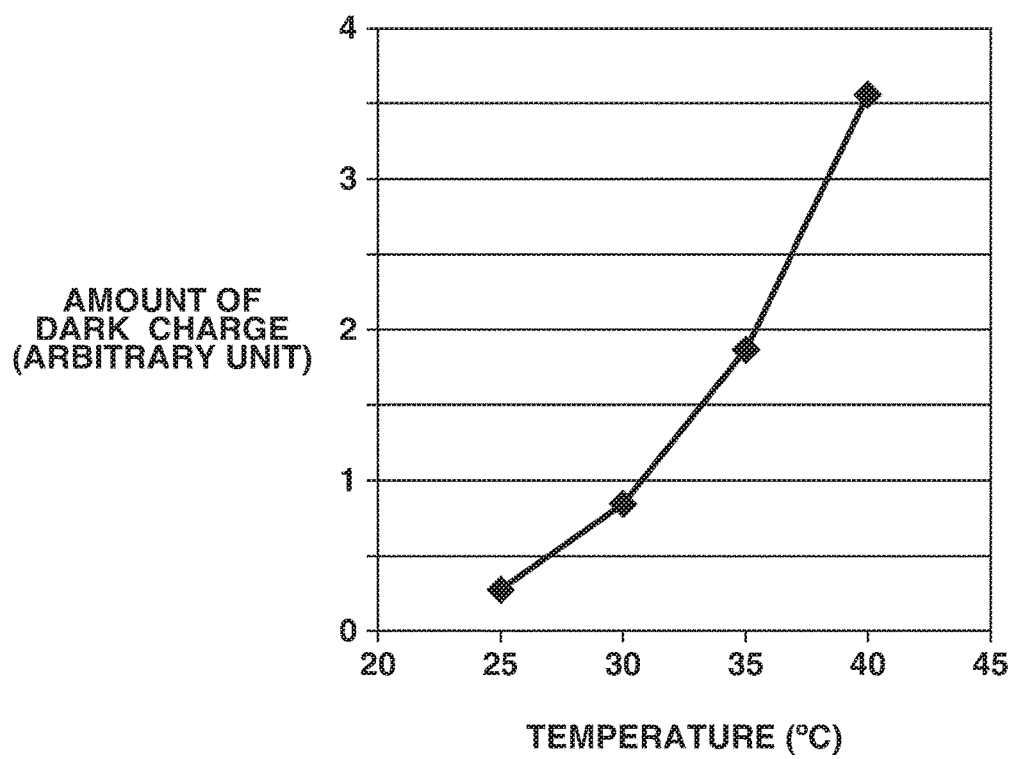
FIGS. 16A and 16B are diagrams illustrating a temperature characteristic of the amount of dark charge and a cross section of a radiation detection apparatus.
Figure 16B:

A radiation detection system according to a fourth exemplary embodiment of the aspect of the present invention has a configuration similar to the radiation detection system according to the second exemplary embodiment. Differences between the present exemplary embodiment and the second exemplary embodiment will be described below. The present exemplary embodiment differs from the second exemplary embodiment in that the plurality of detection pixels 111 also serves as the detection units 91. In the present exemplary embodiment, the control unit 49 detects temperature by using temperature dependence of the amounts of dark charges occurring in the detection pixels 111. FIG. 16 illustrates an example of a temperature characteristic of the amount of dark charge output from a detection pixel 111 which is not irradiated with X-rays, to the detection pixel reading circuit 40. By using such a characteristic that the amount of charge thermally generated in the photodiode 124 of the detection pixel 111 increases with temperature, the amount of dark charges in the detection pixels 111 can be measured to estimate whether the object 2 is opposed to the detection pixels 111 in the neighborhood. Detection pixels 111 opposed to the object 2 increase in temperature because of the body temperature of the object 2, so that the amounts of charges occurring in the detection pixels 111 increase. FIG. 16B illustrates a sectional view of the radiation detection apparatus 4. The sensor substrate 101 is arranged directly bonded to the housing 109 on the opposite side from the scintillator 190 so that the temperature of the object 2 is quickly transmitted to the sensor substrate 101.

The control unit 49 performs processing similar to that of the flowchart of FIG. 12 according to the second exemplary embodiment. Processing different between the present exemplary embodiment and the second exemplary embodiment will be described below. In step S102, as illustrated in FIG. 17A, the operator places the object 2 in contact with the imaging region 90 and positions the radiation source 1. In step S103, the control unit 49 reads two-dimensional information about the amounts of charges (temperature) detected by the detection pixels 111 which are the detection units 91, to obtain the two-dimensional information about the amounts of charges (temperature) illustrated in FIG. 17B. In step S104, as illustrated in FIG. 17C, the control unit 49 recognizes that the body part of the object 2 (body part of the portion opposed to the imaging region 90) is a limb based on the two-dimensional information about the amounts of charges (temperature) of the detection pixels 111 which are the detection units 91. In step S105, the control unit 49 refers to the database, sets regions of interest for the case where the object 2 is a limb in positions indicated by the white circles in FIG. 17D, and sets regions other than the regions of interest to positions indicated by the black circles in FIG. 17D. Specifically, the control unit 49 assumes that the detection regions 80 in the regions other than the regions of interest, which are indicated by the black circles in FIG. 17D, is non-monitoring-target regions, and sets the flags of those detection regions 80 to 0. The detection regions 80 within the regions of interest are assumed to be monitoring target regions, and the flags of such detection regions 80 are maintained at one. The subsequent processing is similar to that of the second exemplary embodiment. In the present exemplary embodiment, one detection region 80 corresponds to one detection unit 91. The control unit 49 uses a total or average of the pieces of temperate information about the detection pixels 111 in each detection region 80.

FIGS. 17A to 17D described above illustrate the example where the object 2 is a limb. FIGS. 17E to 17H illustrate a case in which the object 2 is the chest. FIGS. 17E to 17H correspond to FIGS. 17A to 17D, respectively. More specifically, FIG. 17F illustrates the reading result of the two-dimensional information about the temperature if the object 2 is the chest illustrated in FIG. 17E. In such a case, the control unit 49 determines that the object 2 is the chest (FIG. 17G) and regions of interest (or candidates thereof) are located in the positions of FIG. 17H corresponding to a lung field in chest imaging.

Next, effects of the present exemplary embodiment will be described. In the present exemplary embodiment, the plurality of detection units 91 for detecting temperature is two-dimensionally arranged to correspond to the imaging region 90. Based on the two-dimensional temperature pattern of the detection units 91, regions of interest are identified in advance before radiation irradiation. The present exemplary embodiment provides the same effects as those of the second exemplary embodiment. In addition, according to the present exemplary embodiment, the detection pixels 111 can serve as the detection units 91. This simplifies the configuration of the radiation detection apparatus 4.

The radiation detection apparatuses 4 according to the first to fourth exemplary embodiments are applicable to a radiation detection system typified by a radiation inspection apparatus. The radiation detection system includes, for example, an imaging apparatus including a radiation detection apparatus 4, a signal processing unit including an image processor, a display unit including a display, and a radiation source for generating radiations.

Figure 18:
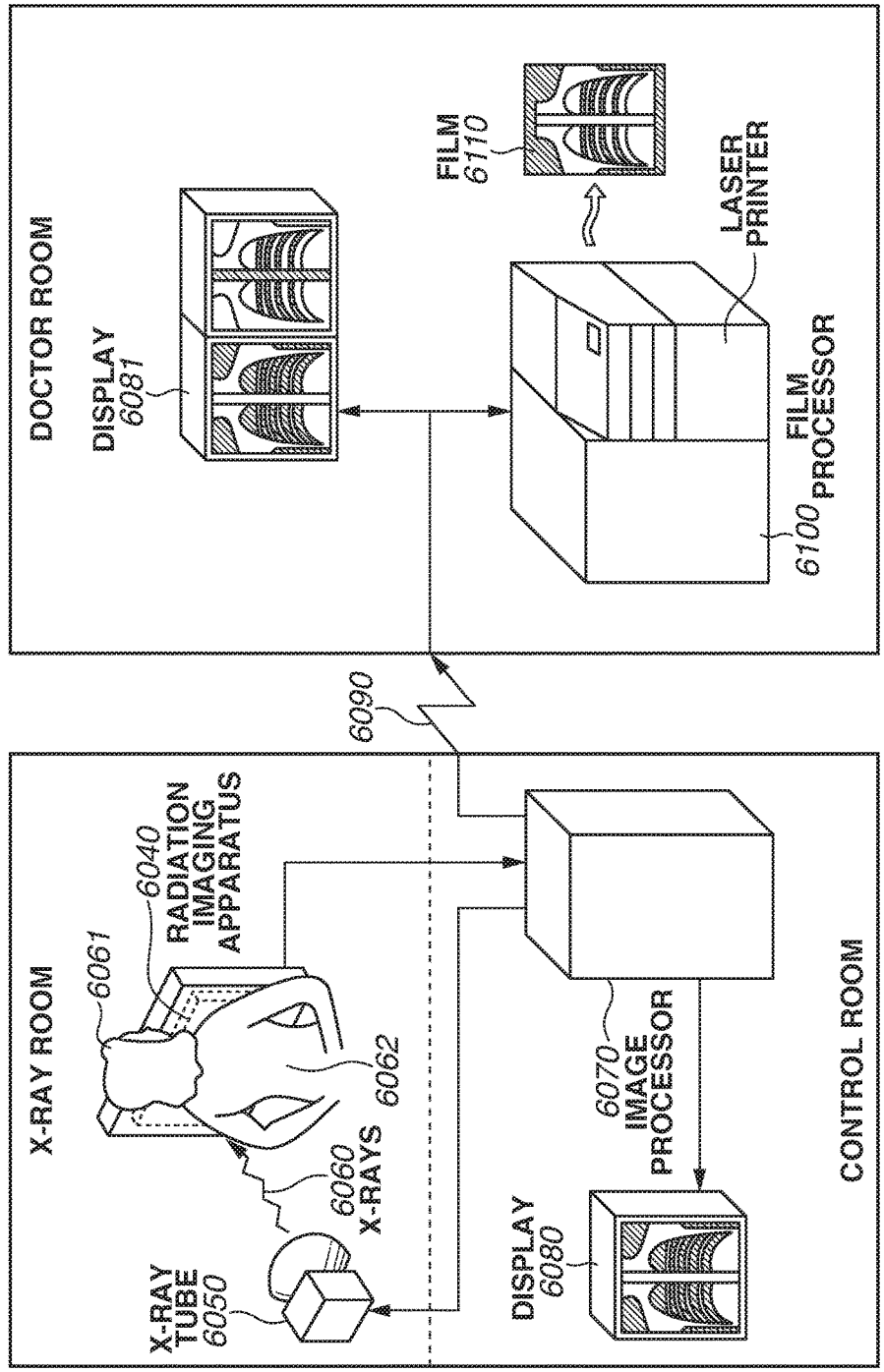
FIG. 18 is a diagram illustrating a configuration example of a radiation detection system.

FIG. 18 is a diagram illustrating an example of a radiation detection system according to a fifth exemplary embodiment of the aspect of the present invention. A radiation imaging apparatus 6040 includes any one of the foregoing detection apparatuses 4. An X-ray tube (radiation source) 6050 generates X-rays (radiations) 6060. The X-rays (radiations) 6060 are passed through the chest 6062 of a subject 6061 such as a patient, and incident on the radiation imaging apparatus 6040. The passed-through incident X-rays 6060 contain information about the interior of the body of the subject 6061. The radiation imaging apparatus 6040 obtains electrical information according to the incident X-rays 6060. The electrical information is then digitally converted, subjected to image processing by the image processor (signal processing unit) 6070, and displayed as an inspection result by the display (display unit) 6080 in a control room. This information is also transferred to a remote place by a network (transmission processing unit) 6090 such as a telephone, a local area network (LAN), and the Internet. The information can thus be displayed as an inspection result on a display 6081 in another place such as a doctor room, and a doctor in the remote place can make a diagnosis. The information and the inspection result can be stored in an optical disk, for example. A film processor 6100 can record the information and the inspection result on a recording medium such as a film 6110.

As described above, in the first to fifth exemplary embodiments, the detection units 91 correspond to the plurality of detection pixels 111, and detect any of light, pressure, capacitance, and temperature as two-dimensional information. Based on the two-dimensional information from the plurality of detection units 91, the control unit 49 narrows down monitoring target regions or regions of interest in advance before the irradiation. Needless operations can thus be eliminated to increase the temporal resolution of the AEC operation. In the first to fifth exemplary embodiment, information about regions other than the regions of interest can be excluded to increase the accuracy of the AEC operation and increase the spatial resolution. The foregoing radiation detection system can be used for a medical image diagnostic apparatus, a nondestructive inspection apparatus, and an analysis apparatus using radiations.

All the foregoing exemplary embodiments illustrate just a few examples of embodiment when putting the aspect of the present invention into practice and the technical scope of the aspect of the present invention is not construed to be limited thereto. An exemplary embodiment of the aspect of the present invention may be carried out in various forms without departing from the technical idea characteristics thereof.

According to an exemplary embodiment of the aspect of the present invention, a radiation irradiation amount can be detected with high temporal and spatial resolutions.

Other Embodiments

Embodiment(s) of the aspect of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the aspect of the embodiments has been described with reference to exemplary embodiments, it is to be understood that the aspect of the embodiments is not limited to the disclosed exemplary embodiments. The scope of the following claims is to be accorded the broadest interpretation so as to encompass all such modifications and equivalent structures and functions.

This application claims the benefit of Japanese Patent Application No. 2015-217746, filed Nov. 5, 2015, which is hereby incorporated by reference herein in its entirety.

What is claimed is:

1. An apparatus comprising:
    a plurality of detection pixels configured to generate a signal according to a radiation irradiation amount to obtain radiation irradiation information;
    a detection unit configured to correspond to a region of the plurality of detection pixels and detect one of light which is irradiated to the apparatus from a visible light source; and
    a control unit configured to determine a monitoring target detection pixel and a non-monitoring-target detection pixel among the plurality of detection pixels based on two-dimensional information, read the signals of detection pixels of a row in which the monitoring target detection pixel is included.

2. The apparatus according to claim 1, wherein the detection unit detects an irradiation field of radiations or a position of an object based on the two-dimensional information, and
    wherein the control unit determines the monitoring target detection pixel and the non-monitoring-target detection pixel among the plurality of detection pixels based on the irradiation field of the radiations or the position of the object, read the signals of the detection pixels of the row in which the monitoring target detection pixel is included, and not read the signals of the detection pixels of a row in which the monitoring target detection pixel is not included.

3. The apparatus according to claim 1, further comprising a plurality of normal pixels configured to generate a signal according to the irradiation amount to generate a two-dimensional image,
    wherein the plurality of detection pixels is arranged in a region of the plurality of normal pixels in order to obtain the radiation irradiation information regarding radiations irradiated when the two-dimensional image is generated by the plurality of normal pixels, and
    wherein the control unit, if a cumulative irradiation amount based on the signals of the detection pixels of the read row exceeds a threshold, outputs an irradiation stop signal and reads the signals of the plurality of normal pixels.

4. The apparatus according to claim 1, further comprising a plurality of normal pixels configured to generate a signal according to the irradiation amount to generate a two-dimensional image,
    wherein the plurality of detection pixels is arranged in a region of the plurality of normal pixels, and
    wherein the control unit, if the read row is a row including a region of interest and the cumulative irradiation amount based on the signals of the detection pixels of the read row exceeds a threshold, outputs an irradiation stop signal and reads the signals of the plurality of normal pixels.

5. The apparatus according to claim 1, wherein the control unit recognizes a body part of an object based on the two-dimensional information, and determines the monitoring target detection pixel and the non-monitoring-target detection pixel among the plurality of detection pixels based on the recognized body part of the object.

6. The apparatus according to claim 1, wherein the plurality of detection pixels also serves as the detection unit.

7. The apparatus according to claim 1, wherein the plurality of detection pixels includes a plurality of switch elements for reading the signals of the plurality of detection pixels, respectively, and
    wherein the control unit brings the switch elements of the detection pixels of the row in which the monitoring target detection pixel is included, into a conducting state on a row-by-row basis, reads the signals of the detection pixels of the row in which the monitoring target detection pixel is included on a row-by-row basis, and maintains the switch elements of the detection pixels of the row in which the monitoring target detection pixel is not included, in a non-conducting state.

8. The apparatus according to claim 1, further comprising a reading circuit configured to process the signal read from the monitoring target detection pixel and to suspend processing of the signal read from the non-monitoring-target detection pixel.

9. The apparatus according to claim 1, wherein the detection unit detects the two-dimensional information before the irradiation, and
    wherein the control unit determines the monitoring target detection pixel and the non-monitoring-target detection pixel among the plurality of detection pixels before the radiation irradiation, and reads the signals of the detection signals of the row in which the monitoring target detection pixel is included during the irradiation.

10. The apparatus according to claim 1, wherein the detection unit detects an irradiation field of radiations or a position of an object.

11. A system comprising:
    the apparatus according to claim 1; and
    a radiation source configured to emit radiations.

12. A method for controlling an apparatus including a plurality of detection pixels configured to generate a signal according to a radiation irradiation amount to obtain radiation irradiation information, and a detection unit configured to correspond to a region of the plurality of detection pixels and detect one of light which is irradiated to the apparatus from a visible light source, the method comprising:
    determining a monitoring target detection pixel and a non-monitoring-target detection pixel among the plurality of detection pixels based on two-dimensional information; and
    reading the signals of detection pixels of a row in which the monitoring target detection pixel is included.

13. The method according to claim 12, further comprising:
    detecting an irradiation field of radiations or a position of an object based on the two-dimensional information;
    determining the monitoring target detection pixel and the non-monitoring-target detection pixel among the plurality of detection pixels based on the irradiation field of the radiations or the position of the object; and
    reading by the control unit the signals of detection pixels of the row in which the monitoring target detection pixel is included, and not reading the signals of detection pixels of a row in which the monitoring target detection pixel is not included.

14. The method according to claim 12, further comprising generating a signal according to the irradiation amount to generate a two-dimensional image by a plurality of normal pixels,
    wherein the plurality of detection pixels is arranged in a region of the plurality of normal pixels in order to obtain the radiation irradiation information regarding radiations irradiated when the two-dimensional image is generated by the plurality of normal pixels, and wherein, if a cumulative irradiation amount based on the signals of the detection pixels of the read row exceeds a threshold, outputting an irradiation stop signal and reading the signals of the plurality of normal pixels.

15. The method according to claim 12, further comprising generating a signal according to the irradiation amount to generate a two-dimensional image by a plurality of normal pixels, wherein the plurality of detection pixels is arranged in a region of the plurality of normal pixels in order to obtain the radiation irradiation information regarding radiations irradiated when the two-dimensional image is generated by the plurality of normal pixels, and wherein, if the read row is a row including a region of interest and the cumulative irradiation amount based on the signals of the detection pixels of the read row exceeds a threshold, outputs an irradiation stop signal and reads the signals of the plurality of normal pixels.

16. The method according to claim 12, further comprising:

recognizing a body part of an object based on the two-dimensional information; and determining the monitoring target detection pixel and the non-monitoring-target detection pixel among the plurality of detection pixels based on the recognized body part of the object.

17. The method according to claim 12, wherein the plurality of detection pixels includes a plurality of switch elements for reading the signals of the plurality of detection pixels, respectively, and wherein the method further comprising:

bringing the switch elements of the detection pixels of the row in which the monitoring target detection pixel is included into a conducting state on a row-by-row basis, reading the signals of the detection pixels of the row in which the monitoring target detection pixel is included on a row-by-row basis, and maintaining the switch elements of the detection pixels of the row in which the monitoring target detection pixel is not included, in a non-conducting state.

18. The method according to claim 12, further comprising processing the signal read from the monitoring target detection pixel and suspending processing of the signal read from the non-monitoring-target detection pixel.

19. The apparatus according to claim 1, wherein the first light is visible light or infrared rays.

20. The apparatus according to claim 1, further comprising a scintillator configured to convert the radiation into the second light, and the first light is not emitted from the scintillator.

* * * * *